United States Patent [19]

Honsik et al.

[11] Patent Number: 4,844,893

[45] Date of Patent: Jul. 4, 1989

[54] EX VIVO EFFECTOR CELL ACTIVATION FOR TARGET CELL KILLING

[75] Inventors: Cyril J. Honsik; Ralph A. Reisfeld, both of La Jolla, Calif.

[73] Assignee: Scripps Clinic and Research Foundation, La Jolla, Calif.

[21] Appl. No.: 916,173

[22] Filed: Oct. 7, 1986

[51] Int. Cl.[4] ............................................ A61K 39/395
[52] U.S. Cl. ...................................... 424/85.8; 424/93; 435/240.2; 530/387; 530/828; 530/388; 530/808
[58] Field of Search ...................... 435/2, 4, 7, 29, 948; 935/107, 108; 424/85, 93; 436/512, 519

[56] References Cited

U.S. PATENT DOCUMENTS 4,444,878 4/1984 Paulus.
4,507,391 3/1985 Pukel et al.
4,675,287 6/1987 Reisfeld .................................. 435/68

OTHER PUBLICATIONS

Honsik, C. J. et al., Proc. Natl. Acad. Sci., U.S.A., 83:7893–7897, (10–1986).
Cheresh, D. A. et al., Proc. Natl. Acad. Sci., U.S.A., 82:5155–5159, (8–1985).
Park, M. M. et al., Cellular Immunology, 84:94–103, (1984).
Mule, J. J. et al., Science, 225:1487–1489, (9–1984).
Rosenberg, S. et al., New Engl. J. Medicine, 313(23):1485–1492, (12–1985).
Perez, P. et al., J. Exper. Med., 163:166–178, (1–1986).
Jung, G. et al., Proc. Natl. Acad. Sci., U.S.A., 83:4479–4483, (6–1986).
Staerz, U. D. et al., Nature, 314:628–631, (4–1985).
Cancer Research, (1984), 44:806–809, Dippold et al.
Natural Immunity and Biological Response, (1985), 4:253, Honsik et al.
Eur. J. Immunol., (1986), 16:263–270, Staerz et al.
Proc. Nat'l Acad. Sci. U.S.A., (1986), 83:1453–1457, Staerz et al.
Proc. Nat'l Acad. Sci. U.S.A., (1985), 82:1242–1246, Houghton et al.

Primary Examiner—Margaret Moskowitz
Assistant Examiner—Jeff. P. Kushan
Attorney, Agent, or Firm—Dressler, Goldsmith, Shore, Sutker & Milnamow, Ltd.

[57] ABSTRACT

A method and composition for killing target cells is disclosed. The method utilizes ex vivo IL-2 activation of leucocyte effector cells and arming the activated leucocyte effectors with monoclonal antibodies whose Fc portions bind to the IL-2-activated effectors and whose paratopic portions immunoreact with an epitope expressed on the surfaces of the target cells. The composition contains a cytolytic amount of the armed, IL-2-activated effector cells dispersed in an aqueous physiologically tolerable diluent medium.

20 Claims, 4 Drawing Sheets

TARGET    EFFECTOR

COVALENT BINDING

LYSIS

T-Fc RECEPTOR BINDING

LYSIS

HYBRID ANTIBODY

LYSIS

E-Fc RECEPTOR BINDING

LYSIS

EX VIVO EFFECTOR CELL ACTIVATION FOR TARGET CELL KILLING

The present invention was made with support of the Government of the United States, and the Government of the United States has certain rights in the invention.

DESCRIPTION

TECHNICAL FIELD

The present invention relates to a cytotoxicity method, and particularly to a method for killing target cells such as tumor cells with antibody-directed, ex vivo-activated effector leucocytes.

BACKGROUND OF THE INVENTION

Neuroectodermal tumors are highly malignant, and include neuroblastomas, small cell cancinoma of the lung, gliomas, neuroblastomas and melanomas. Of the neuroectodermal tumors, neuroblastomas occur during infancy and early childhood. Except for Wilms' tumor, they are the most common retroperitoneal tumors in children. Neuroblastomas arise most commonly in the adrenal medulla, but they may also develop in other sympathetic ganglia within the thorax or abdomen. These tumors metastasize early with widespread involvement of lymph nodes, liver, bone, lung and marrow. The prognosis is often good when the tumor is diagnosed prior to obvious metastasis, but with metastasis, prognosis is poor despite the extensive use of radical surgery, deep X-ray therapy, and chemotherapeutic agents.

Several antigenic determinants have recently been detected on neuroblastoma cells with monoclonal antibodies (Mabs). See Seeger, *Ann. Intern. Med.*, 97, 873 (1982); Wikstrand et al., *Cancer Res.*, 42, 267 (1982); Wikstrand et al., *J. Neuroimmunlogy*, 3, 43 (1982); Eisenbarth et al., *Proc. Natl. Acad. Sci. USA*, 76, 4913 (1979); Liao et al., *Eur. J. Immunol.*, 11, 450 (1981); Seeger et al., *Cancer Res.*, 4, 2714 (1981); Kennett et al., *Advances in Neuroblastoma Research*, p. 209, Raven Press, N.Y. (Evans ed.) (1980); Seeger et al., *J. Immunol.*, 128, 983 (1982); Kemshead et al., *Pediatr. Res.*, 15, 1282 (1981). Gangliosides GD3 and GD2 are among the antigenic determinants detected on neuroblastoma cells.

Gangliosides (sialic acid-bearing glycolipids) are thus rapidly being characterized as tumor markers that are relevant target antigens for monoclonal antibody (Mab)-mediated immunotherapy [Dippold et al. (1983) *Cancer Res.* 44:806–810; Houghten et al. (1985) *Proc. Natl. Acad. Sci. USA* 82:1242–1246; Hellstrom et al. (1985) *Proc. Natl. Acad. Sci., USA* 82:1499–1502; Cheresh et al. (1985) *Proc. Natl. Acad. Sci. USA* 82:5155–5159; Honsik et al. (1985) *Natural Immunity and Biological Response* 4:253; and Steplewski et al. (1985) *Proc. Natl. Acad. Sci. USA* 82:8653–8657].

The disialoganglioside GD3, is expressed preferentially on human melanoma cells [Dippold et al. (1980) *Proc. Natl. Acad. Sci., USA* 77:6114–6118; Cheresh et al. (1984) *Proc. Natl. Acad. Sci., USA* 81:5767–5771], and is an effective target in vitro for both complement-mediated tumor cytolysis and antibody-dependent cellular cytotoxicity (ADCC) by Mabs of the IgG3 subclass [Hellstrom et al. (1985) *Proc. Natl. Acad. Sci., USA* 82:1499–1502; Cheresh et al. (1985) *Proc. Natl. Acad. Sci., USA* 82:5155–5159; and Honsik et al. (1985) *Natural Immunity and Biological Response* 4:253]. Monoclonal antibodies of the IgG3 class directed against GD3 have been reported to effectively suppress the establishment of human melanoma tumors in the xenotransplant nude mouse mode [Hellstrom et al. (1985) *Proc. Natl. Acad. Sci., USA* 82:1499–1502; and Cheresh et al. (1985) Proc. Natl. Acad. Sci., USA 82:5155–5159].

Murine mononuclear splenocytes "armed" with anti-GD3 Mabs were recently reported to eradicate well established and progressively growing human melanoma tumors in nude mice [Honsik et al. (1985) *Natural Immunity and Biological Response* 4:253]. Additionally, Houghten et al. (1985) *Proc. Natl. Acad. Sci., USA* 82:1242–1246, using Mab R24 (IgG3) directed to GD3 (discussed in U.S. Pat. No. 4,507,391), observed major tumor regressions in 3 of 11 melanoma patients treated with that antibody in a Phase I clinical trial. It was also reported in Dippold et al., *Cancer Res.*, 44, 806 (1984), that Mab R24 could kill GD3-containing human melanoma cells in vitro after prolonged exposure (greater than 24 hours) to the antibody suggesting an additional, as yet undefined, mechanism of tumor cell killing. Taken together, these findings demonstrate that the potential therapeutic efficacy of anti-GD3 Mabs warrants further study of ganglioside as immunotherapeutic targets.

The fact that the GD2 antigen was shown to be heavily expressed on most excised melanoma and SCCL tumors, as well as on numerous tumor cell lines, Pukel et al., *J. Exp. Med.*, 155, 1133 (1982) and yet is virtually absent from most normal tissues, suggests that it might be a good target antigen for in vivo specific immunotherapy, and tumor imaging.

In a recent report by Kipps et al., *J. Exp. Med.*, 161, 1 (1985), using isotype switch variants of a Mab directed to an epitope on Class I human histocompatibility antigens, an IgG2a isotype variant was shown to be more effective in directing ADCC than the corresponding IgG1 or an IgG2b variant. Recent work from our own laboratory, Schulz et al. (1985) *J. Exp. Med.* 161:1315–1325, also showed specific cytolysis. That work, using Mab 9.2.27, an IgG2a monoclonal antibody that immunoreacts with a chondritin sulfate proteoglycan that is preferentially expressed on human melanoma cells, illustrated that human melanoma tumors, established and progressively growing in nude mice, could be eradicated by simultaneous injection of that Mab along with a relatively large dose of mononuclear splenocytes. Neither the splenocytes nor the antibodies alone achieved significant tumor regression.

Park et al., *Cellular Immunol.*, 84, 94 (1984), reported that a monoclonal antibody of IgG2b isotype could sensitize K562 human erythroleukemia cells to ADCC-mediated lysis. In that case, it was reported that the Mab accelerated killing of the target cells by large granular lymphocytes known to be enriched in natural killer (NK) cells.

Taken together, the results of these studies indicate that monoclonal antibodies may not only be useful reagents for the immunotherapy of cancer, but also that different Mabs can induce tumor killing by several different or even a combination of effector mechanisms.

Some additional recent reports suggest that mouse monoclonal antibodies are relatively well tolerated in humans and pose minimal risks and few, if any, side effects, Oldham et al., *J. Clin. Oncol.*, 2, 1235 (1984). In using murine Mab 9.2.27, discussed before, to treat melanoma patients, that antibody was shown by the above workers to localize specifically to the tumor site with little if any adverse side effects, but provided no apparent clinical improvement of the disease over the period of time of their study in stage four patients with large tumor burdens.

Another form of anti-tumor immunotherapy involves the exposure of mononuclear lymphocytes to the lymphokine interleukin-2 (IL-2) to generate lymphokine activated killer (LAK) cells [Yron et al. (1980) *J. Immunol.* 125:238-245; Lotze et al. (1981) Cancer Res. 41:4420-4425; Grimm et al. (1982) *J. Exp. Med.* 155:1823-1841; Grimm et al. (1983) *J. Exp. Med.* 158:1356-1361].

For example, Rosenberg et al. reported that the use of recombinant IL-2 (rIL-2)-stimulated human LAK cells in phase I clinical trials resulted in marked tumor regression in several patients with progressively growing neoplasms [Rosenberg et al. (1985) *New Engl. J. Med.* 313:1485-1492]. In those clinical trials, large numbers ($10^{10}$-$10^{11}$) of human peripheral blood leukocytes were subjected to doses of rIL-2 (1000 U/$1.5 \times 10^6$ cells/ml) ex vivo for up to 96 hours before being injected intravenously (i.v.) back into the patients. These individuals then received additional i.v. injections of rIL-2 (up to 100,000 U/kg body weight) during the course of their treatment.

Although some dramatic tumor regressions were observed in several patients with extensive neoplasms, the treatment also produced a number of relatively severe clinical problems. Among those clinical problems were fluid retention, pulmonary edema and occasional respiratory distress requiring intubation. Those problems were a result of the direct toxicity effects of rIL-2 infusions.

In a still more recent report, Rosenberg et al. (1986) *Science* 233:1318-1321, reported use of a three-part modality consisting of (a) an immunosuppressing drug, cyclophosphamide, along with (b) rIL-2-expanded tumor-infiltrating lymphocytes (TIL) obtained from resected tumors and (c) a relatively low dose of rIL-2 to successfully cure twelve mice with MC-38 colon adenocarcinoma of advanced hepatic metastases, and to cure up to 50 percent of mice with advanced pulmonary metastases. The rIL-2 was reportedly administered systemically at 25,000 units three times per day for four days. Those tumors reportedly did not respond to LAK therapy.

Several groups have reported the use of bispecific heteroconjugate (hybrid) antibodies for mediating target cell lysis. For example, Jung et al. (1986) *Proc. Natl. Acad. Sci. USA* 83:4479-4483 reported effective killing of human melanoma target cells that were coated with a bispecific hybrid antibody composed of one paratopic molecule that immunoreacted with an antigen on the target cell and a second paratopic molecule (OKT3, ATCC CRL 8001) that immunoreacted with human T cells. Human T cells previously stimulated by contact with OKT3 were used as the effector cells.

Bevan, Staerz and co-workers have published several papers dealing with the use of bispecific hybrid antibodies to kill target cells in murine systems. For example, Staerz et al. (1985) *Nature* 314:628-631 reported use of a hybrid antibody one of whose paratopic portions immunoreacted with an allotypic epitope on the T cell receptor of about 25 percent of peripheral T lymphocytes and the other of whose paratopic portions immunoreacted with the Thy-1.1 alloantigen. That report showed that target S. AKR lymphoma cells that expressed the Thy-1.1 alloantigen were killed by coating the target cells with the bispecific hybrid antibody and subsequent admixture of the coated target cells with various dilutions of cytotoxic T lymphocytes bearing the antigen recognized by the other paratopic portion of the hybrid. Potential target cells that did not bear the Thy-1.1 antigen were not killed. Related studies by that group can be found in Staerz and Bevan (1986) *Proc. Natl. Acad. Sci. USA*, 83:1453-1457; Staerz and Bevan (1986) *Eur. J. Immunol.*, 16:263-270; and Staerz and Bevan (1985) *Eur. J. Immunol.*, 15:1172-1177.

Still further, Perez et al. (1986) *J. Exp. Med.* 163:166-178 described a bispecific heteroconjugate antibody that reportedly targets rIL-2-activated peripheral blood mononuclear cells (PBMCs) to tissue. Thus, one portion of that heteroconjugate binds through its paratope [Fab fragment of Mab OKT3 (ATCC CRL 8001)] to the activated PBMCs, while the other paratope of the heteroconjugate (Fab fragment of a target-binding Mab) binds to the target tissue.

In their study, Perez et al. depleted the lymphocyte effector cell population of monocytes as well as Leu-11-positive (Leu 11+) cells. They reported that their IL-2-activated effectors exhibited the T8 antigen (were T8+) and that elimination of T8+cells using Mab OKT8 (ATCC CRL 8014) and complement eliminated cytoxicity. Removal of T4+ cells by a similar strategy [Mab OKT4 (ATCC CRL 8002) plus complement] increased lysis in the presence and absence of IL-2 activation. Those authors also reported the loss of about one-half of the lytic activity when activated, hybrid antibody-coated effectors were maintained free of IL-2 between 8 and 24 hours.

Bispecific heterobifunctional monoclonal paratopic molecules and methods of their preparation are also disclosed in U.S. Pat. No. 4,444,878 and PCT/US82/01766 (WO 83/02285), whose disclosures are incorporated herein by reference. The techniques described in U.S. Pat. No. 4,350,626 for linking Fab portions of anti-tumor antibodies to the ricin A subunit can also be utilized for linking Fab portions of desired antibodies in the preparation of bispecific hybrids.

BRIEF SUMMARY OF THE INVENTION

The present invention contemplates a method for killing target cells and a composition useful in the method. The method utilizes effector cells that are activated ex vivo, freed from the activating agent, armed with antibodies that immunoreact with the target cells and thereafter co-incubated with target cells.

Thus, one aspect of the invention contemplates a method of specifically killing target cells and comprises the steps of:

(a) Activating ex vivo a culture of leucocytes such as peripheral blood mononuclear cells (PBMCs) or peripheral blood lymphocytes (PBLs) that contain IgG1, IgG2a, IgG2b, or IgG3 antibody Fc receptors with an amount of interleukin-2 (IL-2) sufficient to enhance the natural killer activity of those cells and form IL-2-activitated effector cells.

(b) The IL-2-activated effectors are then separated from toxic amounts of IL-2, and the IL-2-freed cells are collected.

(c) The Fc receptors of those IL-2-activated effector cells are then bound with monoclonal antibodies (Mabs) of class IgG1, IgG2a, IgG2b, or IgG3 Fc portions, to form armed, IL-2-activated effector cells. The paratopic portions of useful Mabs bind to (immunoreact with) an antigen expressed on the surface of target cells.

(d) A cytotoxic amount of the armed, IL-2-activated effector cells is contacted with target cells.

(e) That contact is maintained for a time period sufficient to kill the target cells. This method is useful both in vitro and in vivo. The contact and maintenance steps are carried out out in the substantial absence of exogeneously supplied IL-2.

Another embodiment of the above method contemplates contacting the target cells with a cytolytic amount of bispecific hybrid monoclonal paratopic molecules that contain a first anti-T3 paratopic portion that immunoreacts with the T3 antigen expressed on the surfaces of T cells and a second paratopic portion that immunoreacts with a second epitope expressed on the surface of the target cells. That second target cell epitope is different from the antigen bound by the above, first-named Mabs, and the immunoreaction of those first-named Mabs does not interfere with the immunoreaction of the second paratopic portion of the bispecific hybrid molecules, or vice versa.

The bispecific hybrid molecules can be contacted with the target cells before, substantually simultaneously, or after the contact with the armed, IL-2-activated effector cells. Preferably, that contact is substantially simultaneous with contact by the armed, IL-2-activated effectors. Most preferably, the bispecific hybrid molecules are coated on the surfaces of anti-T3-activated T cells that express the T3 antigen prior to contacting the target cells, and those hybrid-coated or -armed anti-T3-activated T cells are present along with the armed, IL-2-activated effector cells.

Another aspect of this invention contemplates a target cell killing composition. That composition comprises an aqueous physiologically tolerable diluent medium that contains dispersed therein armed, IL-2-activated effector cells from a leucocyte population in an amount effective to kill target cells (a cytolytic amount). The IL-2-activated effector cells are armed with monoclonal antibodies of class IgG1, IgG2a, IgG2b, or IgG3 that are bound to the Fc receptors of the activated cells, and whose paratopic portions immunoreact with an antigen expressed on the surfaces of the target cells.

The composition can also contain a cytotoxic amount of bispecific hybrid monoclonal paratopic molecules that contain first anti-T3 paratopic portions that immunoreact with the T3 antigen expressed on the surfaces of T cells and second paratopic portions that immunoreact with a second epitope expressed on the surface of the target cells, as discussed before. Preferably, the bispecific molecules are present in the composition coated on the surfaces of anti-T3-activited T cells as armed, anti-T3-activated T cells.

The present invention has several benefits and advantages. Salient among those benefits and advantages is that a leucocyte population can be activated and armed ex vivo and then utilized to kill target cells in the absence of exogeneously supplied IL-2, thereby avoiding the toxicity problems associated with administration of exogeneously supplied IL-2 to a recipient animal.

Still further benefits and advantages of the invention will be apparent from the description of the invention that follows.

BRIEF DESCRIPTION OF THE DRAWINGS

In the Figures forming a portion of this disclosure.

Figure 1A:
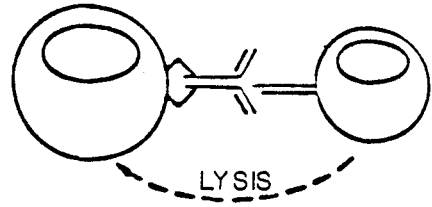
FIG. 1 is a schematic representation of various strategies of target cell lysis mediated by antibodies (the Y-shaped entity) and an effector cells. In strategy A, a monoclonal antibody that immunoreacts with an epitope on the effector cell such as the T cell receptor is depicted as being covalently linked to the surface of the target cell. Strategy B illustrates a monoclonal antibody that immunoreacts with an effector cell epitope complexed with the target cell via the Fc receptor of the target cell (T-Fc binding). Strategy C illustrates the use of a heterobifunctional hybrid monoclonal antibody that immunoreacts with an epitope on the target cell and with an epitope on the effector cell; the two portions of the hybrid antibody are illustrated by wider and narrower lines. Aspects of strategy C can be utilized herein. Strategy D illustrates the use of a monoclonal antibody that immunoreacts with an epitope on the target molecule and is complexed to the effector cell via the Fc receptor of the effector cell (E-Fc binding). Strategy D is the principal strategy utilized in the invention discussed herein. This figure is adapted from Staerz et al., "Targeting for T-Lymphocyte-Mediated Lysis by Hybrid Antibodies" in *Cytolytic Lymphocytes and Complement*, E. Podack, ed., CRC Press, Boca Raton, Fla. (in press).
Figure 1B:
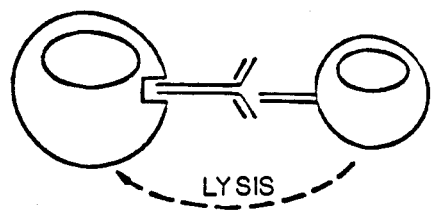

(open bars). The percentage of specific lysis shown was obtained after subtraction of values for NK lysis.

DETAILED DESCRIPTION OF THE INVENTION

I. DEFINITIONS

The term "antibody" refers to a molecule that is a member of a family of glycosylated proteins called immunoglobulins that can specifically combine with an antigen. Such an antibody combines with its antigen by a specific immunologic binding interaction between the antigenic determinant (epitope) of the antigen and the antibody combining site (paratope) of the antibody.

An "antibody combining site" is that structural portion of an antibody molecule comprised of heavy and light chain variable and hypervariable regions that specifically binds antigen. Using the nomenclature of Jerne, *Ann. Immunol. (Inst. Pasteur)*, 125C, 373 (1974) an antibody combining site is usually referred to herein as a "paratope".

The word "antigen" has been used historically to designate an entity that is bound by an antibody, and also to designate the entity that induces the production of the antibody. More current usage limits the meaning of antigen to that entity bound by an antibody, whereas the word "immunogen" is used for the entity that induces antibody production. Where an entity discussed herein is both immunogenic and antigenic, it will generally be termed an antigen.

The phrase "antigenic determinant" refers to the actual structural portion of the antigen that is immunologically bound by an antibody combining site. The Jerne nomenclature defines an antigenic determinant as an "epitope".

The term "biologically active" refers at least to the ability to specifically bind antigen or specific antibody combining site, although other general or effector capability may be present as well. Biological activity of a paratopic molecule containing an antibody combining site is evidenced by the immunologic reaction of the antibody paratope (combining site) with its epitope (antigenic determinant) upon their admixture in an aqueous medium to form an immunoreactant, at least at physiological pH values and ionic strengths. Preferably, biological activity occurs under biological conditions; i.e., those conditions wherein a paratope-containing molecule of this invention binds to its epitope within a pH value range of about 5 to about 9, at ionic strengths such as that of distilled water to that of about one molar sodium chloride, and at temperatures of about 4 degrees C. to about 45 degrees C. The monoclonal paratopic molecules useful herein are biologically active.

"ELISA" refers to an enzyme-linked immunosorbent assay that employs an antigen or antibody bound to a solid phase and an enzyme-antibody or enzyme-antigen conjugate to detect and quantify the amount of antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are incorporated herein by reference.

"Enzyme" refers to a protein capable of accelerating or producing by catalytic action some change in a substrate for which it is often specific.

"Immunoreactant" as used herein refers to the product of an immunological reaction; i.e., that entity produced when an antigen is immunologically bound by an antibody or a molecule containing a paratope. An immunoreactant is therefore a specific type of complex formed between molecules.

The term "intact antibody" is used herein to distinguish a complete molecule secreted by a cell from other, smaller, molecules that also contain the paratope necessary for biological activity in an immunoreaction with an antigen.

The paratopic molecules useful in the present invention are monoclonal paratopic molecules. A "monoclonal antibody" (often referred to herein as a "Mab") is a antibody produced by clones of a hybridoma that secretes but one kind of antibody molecule, and a monoclonal paratopic molecule is a monoclonal antibody. The hybridoma cell is fused from an antibody-producing cell and a myeloma or other self-perpetuating cell line. Such antibodies were first described by Kohler and Milstein, *Nature*, 256, 495–497 (1975), which description is incorporated herein by reference.

The terms "monoclonal paratopic molecule", "paratopic molecule", "monoclonal antibody" and "Mab" are used interchangeably herein to refer to an intact monoclonal antibody.

The words "secrete" and "produce" are often used interchangeably in the art as to cells from which antibody molecules are obtained. Cells that produce antibodies may, however, not secrete those molecules into their environment. The hybridoma cells of interest herein secrete monoclonal antibodies into their environment. Nevertheless, such cells are sometimes referred to herein as "antibody-producing" cells, and their antibodies are sometimes referred to as being "produced" in keeping with the phrase utilized in the art.

The term "supernatant" is used herein to refer to the in vitro liquid medium in which cells are cultured. Monoclonal paratopic molecules produced by the hybridoma cultures of interest herein are secreted into their culture medium environment. Therefore the culture medium supernatant is one preferred source of the monoclonal paratopic molecules and is readily obtainable free from hybridoma cells by well known techniques. Exemplary of such techniques is low speed centrifugation to sediment cells out of the liquid medium. Monoclonal paratopic molecules can alternatively be obtained from ascites tumor fluid (ascites fluid) of laboratory animals into which the hybridoma tissue was introduced. Both methods are described hereinafter.

II. GENERAL DISCUSSION

As already noted, several strategies have been developed to obtain cytolysis. Treatments such as systemic administration of rIL-2 and the sole use of LAK cells produced by activation with rIL-2 have been shown to be too non-specific for generalized use. The more recently reported results with TIL cells and IL-2 is reportedly effective in mice, but still utilizes systemic administration of rIL-2. Since IL-2 can be toxic, it would be beneficial if such systemic uses could be avoided.

As also pointed out previously, the exquisite specificity of monoclonal antibodies has been brought to bear upon cytolysis of pre-specified target cell populations. However, when used as the only modality, results with monoclonals alone have been uneven.

Four strategies that utilize target-cell specific Mabs along with effector cells are illustrated schematically in FIG. 1. Strategy A of that Figure illustrates use of Mabs whose paratopic portions immunoreact with an epitope on the effector cell and whose Fc portions are covalently linked to the target cell. Strategy B utilizes Fc receptors on the target cell to bind to the antibody (T-Fc receptor binding), while the paratope binds to the effector cell. Strategy C utilizes a hybrid monoclonal antibody, a first paratopic portion of which immunoreacts with the effector cell whereas the second paratopic portion immunoreacts with the target cell. Aspects of Strategy C are useful herein as part of combined modality with Strategy D. Strategy D binds the Fc portion of an IgG1, IgG2a, IgG2b or IgG3 antibody to a receptor on the effector cell (E-Fc receptor binding), whereas the antibody paratope immunoreacts with an epitope on the target cell.

The present invention utilizes the general concept of strategy D of FIG. 1 as an aspect of a principal modality in killing target cells. The studies on which the invention is based were deigned to obtain alternative procedures to those now in use to produce less severe clinical problems than those discussed previously as to the systemic administration of IL-2, while obtaining the objective of specifically lysing target cells such as tumor cells. As is shown illustratively hereinafter, the present method "arms" and specifically targets IL-2-activated leucocytes such as peripheral blood mononuclear cells (PBMCs) with Mabs directed to antigens such as GD2 and GD3 that are preferentially expressed at high densities on target cells such as melanoma or neuroblastoma tumor cells.

The results here show that a brief (15-minute to 4-hour) ex vivo co-incubation (admixture, contact and maintenance) of human leucocytes such as PBMCs with a low dose of rIL-2 augments both natural killing (NK), and particularly augments antibody-dependent cellular cytotoxicity (ADCC) of human melanoma and neuroblastoma target cells. Additionally, the illustrative results here show that the disialogangliosides GD2 and GD3 represent effective target structures on human melanoma as well as neuroblastoma cells for Mab-targeted, activated human PBMCs. Furthermore, these Mab-armed and rIL-2-activated effector cells can specifically distinguish chemically-defined GD2 and GD3 disialoglioside target structures.

One aspect of the present invention is directed to a method of specifically killing target cells; i.e., cells desired to be killed that express a particular antigen on their surfaces. Exemplary of such cells are tumor cells that express gangliosides GD2 and/or GD3 on their surfaces as antigens. Such cells are used illustratively herein as target cells with the understanding that they are exemplary of such target cells.

Additional exemplary target cells, their surface antigens and immunoreacting Mabs are discussed hereinafter. It is to be understood that for in vivo treatments, it is preferred that the target cells such as tumor cells preferentially express the antigen bound by the Mabs so that lysis of normal cells is minimized. Put differently, the antigen on the target cells with which the Mab immunoreacts is substantially absent from non-target cells, or non-target cells are substantially free of the antigen with which the Mab immunoreacts.

In accordance with this method, a leucocyte population such as peripheral blood mononuclear cells (PBMCs) that contain a receptor for IgG1, IgG2a, IgG2b or IgG3 antibodies is cultured ex vivo in an aqueous medium with an amount of interleukin-2 sufficient to enhance the natural killer (NK) activity of those cells to form IL-2-activated effector cells. Those activated effector cells are thereafter freed of (separated from) toxic amounts of IL-2, as by rinsing.

The Fc receptors of the IL-2-activated effector cells are bound to (coated with) Fc-containing monoclonal antibodies of class IgG1, IgG2a, IgG2b or IgG3 that immunoreact with an antigen expressed on the surface of target cells to form armed, IL-2-activated effector cells. The armed, IL-2-activated effector cells are then admixed and contacted with the target cells. That admixture is maintained for a time period sufficient for the monoclonal antibody-armed, IL-2-activated effector cells to kill the target cells.

The leucocytes utilized can be autologous; i.e., from the same animal as the tumor cells, or can be from another compatible animal so long as those cells do not cause an adverse immunological response when admixed with the target cells. The leucocytes utilized can be obtained from serum or plasma without further separations into more narrowly defined cell populations.

Where more specific leucocyte sub-populations are desired, the leucocytes can be fractionation by Ficoll-Hypaque density gradient centrifugation to provide PBMCs, or by discontinuous Percoll gradient centrifugation of peripheral blood lymphocytes (PBLs) to provide a cell population enriched in large granular lymphocytes (LGL). LGL exhibit the Leu-11 antigen also found on NK cells and neutrophils. Such cells are referred to as Leu-11+. Other, still more narrowly defined effector cell populations can be obtained as are desired using known techniques. PBMC and PBL populations are themselves partially enriched in potentially activated effectors, and are utilized herein as exemplary leucocyte populations from which activated effector cells are obtained.

The normal leucocyte population includes IL-2-activatable effector cells that contain receptors capable of binding IgG1, IgG2a, IgG2b or IgG3 Fc portions of antibodies. Thus, special selection of leucocytes for the presence of the desired receptors is generally not required. In addition, as the results discussed hereinafter show, appropriate leucocytes are present in PBMCs of normal, asymptomatic persons, as well as being present in PBMCs of patients having tumor cells to be attacked and lysed.

It is noted that a greater population of activatable effector cells is normally present that contain receptors for IgG2a, IgG2b, or IgG3 Fc portions than for IgG1 Fc portions. Consequentially, Mabs containing IgG2a, IgG2b or IgG3 are preferred as are activatable effector cells that contain receptors for the Fc portions of such monoclonals.

The leucocytes such as PBMCs are cultured ex vivo under usual cell culture conditions for such mammalian cells. An exemplary culture technique and culture medium are discussed in the Materials and Methods Section. Typically, however, such cells are cultured at a concentration of about $5 \times 10^5$ to about $5 \times 10^6$ cells per milliliter (cells/ml).

The leucocytes are activated by culturing with an amount of interleukin-2 sufficient to enhance ADCC and NK activities of those cells to form IL-2-activated effectors. Natural IL-2 can be obtained and is useful herein. See for example, U.S. Pat. No. 4,473,642. However, recombinant IL-2 (rIL-2) is more readily available and is effective for the present purposes.

Figure 2:
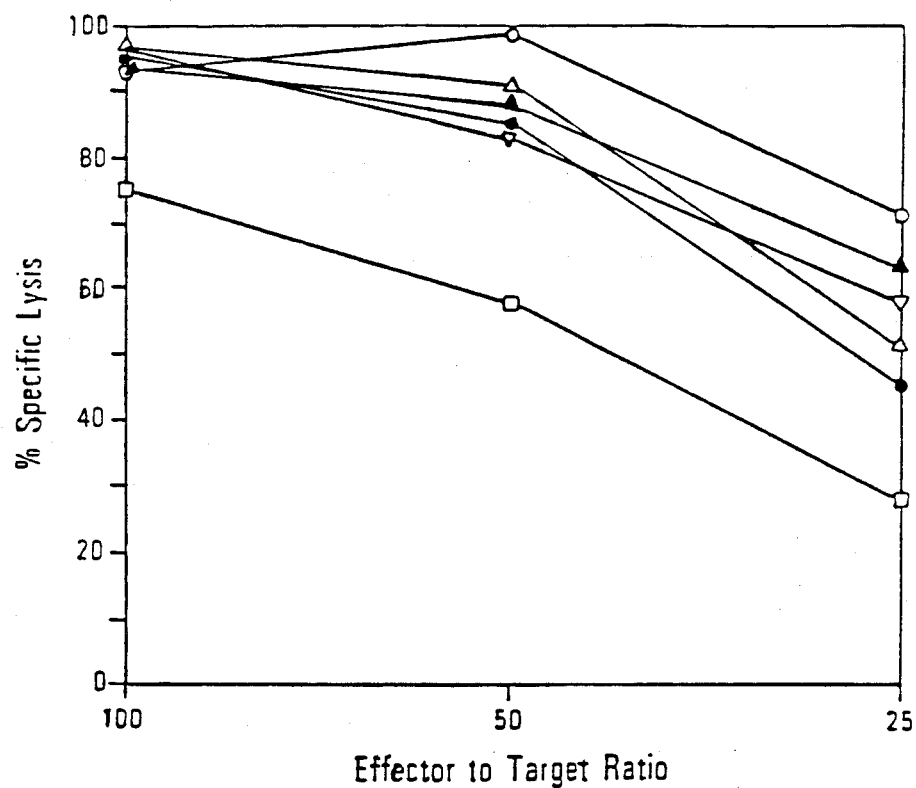
FIG. 2 is a graph illustrating augmentation of antibody-dependent cellular cytotoxicity (ADCC) induced by short-term ex vivo activation of human peripheral blood mononuclear cells (PBMCs) with recombinant interleukin-2 (rIL-2) on $^{51}$Cr-labeled M21 human melanoma cells in vitro. Human PBMCs at $10^6$ cells per milliliter (cells/ml) were activated by admixture with 250 units/milliliter (U/ml) of rIL-2 at 37 degrees C. for different time periods. The PBMCs were thereafter washed substantially free of toxic amounts of rIL-2 and admixed with Mab 11C64 and target M21 cells at the effector to target cell ratios (E:T) shown on the abscissa. The ordinate is in units of percent specific lysis of the target cells. Quadruplicate determinations were made for each point with standard deviations of less than about 10 percent. The ex vivo activation times utilized were as follows: No rIL-2 (□); 15 minutes of rIL-2 activation ( ); 30 minutes of rIL-2 activation ( ); 1 hour of activation (Δ); 2 hours of activation ( ); and 4 hours of activation (O).

The culturing conditions here are again those usually used in the art for mammalian cells, and such cultures are typically carried out at 37 degrees C. The amount of rIL-2 used does not appear to be of great criticality so long as a minimal amount is used with a minimal culture time. For example, as shown in Table 4, hereinafter, there was little difference in ADCC over a range of 50 through 50,000 U/ml of rIL-2 when a four-hour, 37 degrees C. culture technique was utilized with a 6:1 to 50:1 effector to target cell (E:T) ratio and 10⁶ PBMCs. However, less than 50 U/ml rIL-2 was found to be ineffective under the same conditions. In addition, as shown in FIG. 2, suitable activation can be achieved in as little as about 15 minutes of culture with rIL-2. Appropriate ex vivo activation regimens can thus be readily obtained by a skilled worker.

IL-2-Activation of effector cells can also be ascertained by determining the NK activity of the cell population sought to be activated against a standard target cell line. The M21 melanoma cell line is one such line as are the human melanoma SK-MEL-28 (ATCC HTB 72) and WM 266-4 (ATCC CRL 1676) cell lines. Typically, using PBMCs, IL-2-activated effector cells have about twice the NK activity of a similar number of non-activated PBMCs when utilized at the same E:T ratios against a predetermined amount of standard target cells. Thus, a relatively simple test can be used as an external control to determine whether the leucocytes are activated. A standard prepared from leucocytes of a normal, asymptomatic animal that are known not to be activated can be used to assure that the initially used leucocytes are not themselves activated effectors.

The armed, IL-2-activated effector cells are formed by admixture of the activated effector cells with an effective amount of the appropriate Mab to bind the Mab Fc portions to the Fc receptors of the activated effectors. This process is sometimes referred to herein as "coating" the effectors. The Mabs utilized are usually purified prior to coating, and can be so prepared by any of a number of well known techniques.

In typical preparations, the PBMCs are activated with rIL-2, separated substantially free of toxic amounts of rIL-2 as by washing, and then admixed and contacted with the Mabs in an appropriate aqueous medium. The admixture so formed is maintained for a period of time sufficient for the antibody Fc portions to react with (complex with) the Fc receptors on the surfaces of the IL-2-activated effector cells to form Mab-armed, IL-2-activated effector cells. Typical admixture, contact and maintenance (co-incubation) times for arming effector cells with Mabs are about 5 minutes to about 24 hours, and more preferably about 5 to about 60 minutes, at a temperature of about 0 to about 40 degrees C., and more preferably at about 37 degrees C.

An excess of Mab expected to be bound over the amount of Fc receptor-bearing cells is normally utilized to achieve optimal coating of the effector calls. Because the before-mentioned reports of the use of murine monoclonals in human systems have indicated little or no adverse reaction when such Mabs were introduced into humans, an excess of murine Mabs can be utilized, and that excess need not be freed (separated) from the armed, IL-2-activated effectors. However, such a separation can readily be effected by usual centrifugation and washing procedures. If desired, the IL-2-activated effector cells can be separated from the IL-2 after they are armed, thereby utilizing one fewer washing step so that IL-2 and excess Mabs (where used) are separated from the armed, IL-2-activated effectors in one step.

An effective, cytotoxic, amount of the Mab-armed, IL-2-activated effector cells so formed are then admixed and contacted with target cells such as tumor cells, in the substantial absence of exogenously supplied IL-2. Both the target and effector cells are typically in aqueous media when they are admixed. The aqueous medium of the Mab-armed, IL-2-activated effectors is typically a growth or other medium such as DMEM or PBS. The aqueous medium for the target cells can be a similar medium when the contacting is carried out in vitro, and is the blood and other usual bodily fluids when the contacting is carried out in vivo.

The contact between the armed, IL-2-activated effectors and target cells is maintained in the absence of exogenously supplied IL-2 and under biological conditions, as discussed before, for a time period sufficient for the armed, IL-2-activated effector cells to kill (lyse) the target cells. The maintenance time of the contact in vitro is typically about 1 to about 6 hours, with a 4-hour time period being utilized herein as exemplary. For in vivo administration, the contact is maintained for a time period sufficient for the armed effectors of the composition introduced into the animal the Mab-armed, IL-2-activated effector cells plus the aqueous medium as a physilogically tolerable diluent) to be cleared by normal bodily functions of the recipient animal.

In vitro lysis of the target cells can readily be observed by utilization of a radioactive label such as $^{51}Cr$, as is used herein. For in vivo treatments or recipient animals such as mice, rats, guinea pigs or humans, reduction in tumor burden as ascertained by usual techniques provides a convenient assay. Serological or other assays for an increased amount of target cell antigen are also useful means for ascertaining the killing of target cells.

Table 1, below, lists exemplary monoclonal antibodies useful in the present invention. Those Mabs are listed by the name utilized in a publication, by the reported ATCC accession number (ATCC No.) of their hybridomas, the antibody class, and the antigen with which the Mab reportedly immunoreactants. A citation to a discussion of each Mab and its immunoreactivity is provided by the footnote under the antigen listing.

TABLE 1

| Exemplary Mabs | | | |
|---|---|---|---|
| Mab | ATCC No. | Class | Antigen |
| MB 3.6 | HB 8890 | IgG3 | GD3[1] |
| 14.18 | HB 9118 | IgG3 | GD2[2] |
| 11C64 | — | IgG3 | GD3[3] |
| 9.2.27 | — | IgG2a | condritin sulfate proteoglycan[4] |
| R 24 | — | IgG3 | GD3[5] |
| HT29/26 | HB 8247 | IgG2a | colon cancer[6] glycoprotein gp 29 |
| HT29/36 | HB 8248 | IgG3 | colon cancer[6] glycoprotein gp 29 |
| CLT85 | HB 8240 | IgG1 | colon cancer[6] |
| F64.5 | — | IgG2a | mammary carcinoma[7] |
| B38.1 | — | IgG1 | pancarcinoma 70 kd protein[7] |
| 6A2 | HB 8112 | IgG3 | 39 kd Hib outer membrane protein[8] |
| 2E10 | — | IgG2a | 45 kd Hib |

TABLE 1-continued

| Mab | ATCC No. | Class | Antigen |
|---|---|---|---|
| 8F8 | — | IgG3 | outer membrane protein[8] 39 kd Hib outer membrane protein[8] |
| 17A10 | — | IgG2a | 39 kd Hib outer membrane protein[8] |
| 16C2 | — | IgG2b | 37 kd Hib outer membrane protein[8] |
| F36/22 | HB 8215 | IgG3 | human breast carcinoma[9] |
| T16 | HB 8279 | IgG2b | human bladder tumor, glycoprotein gp48[10] |
| T101 | HB 8273 | IgG2a | human bladder tumor[10] |
| 1116-NS-19-9 | HB 8059 | IgG1 | colorectal carcinoma monosialo-ganglioside[11] |

[1]Cheresh et al. (1985) Proc. Natl. Acad. Sci. USA 82:5155-5159; and Cheresh et al. (1984) Proc. Natl. Acad. Sci. USA 81:5767-5771.
[2]Cheresh et al. (1986) Cancer Res. 44:5112-5118.
[3]Cheresh et al. (1986) J. Cell. Biol. 102:688.
[4]Bumol et al. (1982) Proc. Natl. Acad. Sci. USA 79:1245; and Harper et al. (1984) J. Immunol. 132:2096.
[5]U.S. Pat. No. 4,507,391.
[6]U.S. Pat. No. 4,579,827.
[7]U.S. Pat. No. 4,522,918.
[8]U.S. Pat. No. 4,455,296. Hib = Haemophilus influenzae type b.
[9]European Patent Application No. 84400420.0, publication No. 0 118 365, published September 12, 1984.
[10]European Patent Application No. 84102517.4, publication No. 0 118 891, published September 19, 1984.
[11]U.S. Pat. No. 4,471,057.

It must be understood that the present method and results obtained by its use are unexpectedly different from the results obtained from utilization of a Mab alone, IL-2-activated PBMCs alone or from unactivated PBMCs and an appropriate Mab. The startling difference in result is shown particularly in the in vivo work discussed hereinafter related to Table 6.

It also was unexpected that after IL-2-activation, the presence of additional IL-2 was not required during target cell lysis. See for example, Table 5.

The exact mechanism by which the present invention operates is unknown. As is discussed hereinafter, at least enhanced antibody-dependent cellular cytotoxicity (ADCC) as schematically illustrated in FIG. 1D is thought to play a significant role, as does enhanced natural killer (NK) activity. Whether one or more additional mechanisms is involved is unclear. The results obtained in some studies, particularly the in vivo study discussed hereinafter, appear to be synergistic, and cytolytic results greater than the sum of the results obtained by IL-2-induced NK activity and normal ADCC were observed.

An aqueous composition that contains an effective, cytotoxic amount of the Mab-armed, Il-2-activated effector cells dispersed in a physiolgically tolerable diluent aqueous medium constitutes another aspect of the invention. Exemplary aqueous media include water, normal saline, PBS, Ringer's solution, lactated Ringer's solution, and the like.

An effective, cytotoxic amount of the armed, activated effector cells can vary between in vitro and in vivo uses, as well with the amount of target cells, target cell type, the particular assay used and the contact time and temperature. For in vitro cytotoxicity, an effector to target cell ratio (E:T) of about 5:1 to about 500:1 is suitable with a ratio of about 25:1 to about 100:1 being preferable.

For in vivo cytotoxicity, about $1 \times 10^8$ to about $1 \times 10^{10}$, and more preferably about $1 \times 10^9$ to about $5 \times 10^9$, armed, activated effector cells, calculated as a PBMC population, are utilized for adult humans, whereas about $5 \times 10^6$ to about $5 \times 10^7$ cells are used in mice. Such cells are typically prepared using about 200 to about 400 micrograms (ug) of purified Mab per about $1 \times 10^7$ to about $2 \times 10^7$ cells, as discussed hereinbefore. Admixture of the Mabs with the effector cells is typically carried out at about 0.025 to about 5 milligrams per milliliter (mg/ml), and more preferably at about 0.5 to about 2 mg/ml, of Mab with about $1 \times 10^6$ to about $1 \times 10^8$ cells/ml, more preferably about $1 \times 10^7$ to about $5 \times 10^7$ cells/ml, with lower concentrations of Mab being used with lower cell concentrations, and vice versa.

A composition of the invention is typically administered as a unit dose in the before-described method, particularly where in vivo treatments are utilized. The term "unit dose" refers to physically discrete units suitable as unitary dosages for animals, each unit containing a predetermined quantity of armed, activated effector cells calculated to produce the desired therapeutic effect in association with the physiologically tolerable aqueous medium as diluent.

Yet another aspect of the present invention utilizes a combined modality of the before-described method along with bispecific or heterobifunctional hybrid monoclonal paratopic molecules (usually referred to herein as bispecific hybrid molecules or hybrids) and activated effector cells. Methods of preparing such bispecific hybrid molecules are discussed in the before-metioned papers and patents, and will not be dealt with further herein.

Figure 1C:
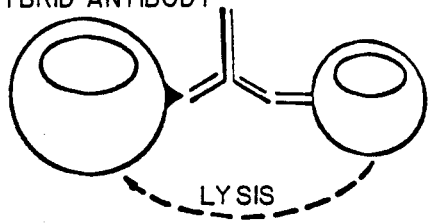
Figure 1D:
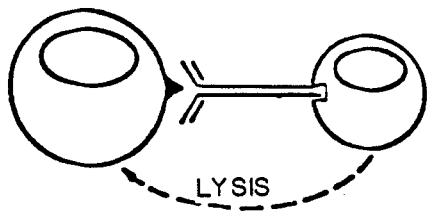

The bispecific hybrid molecules useful in this aspect of the invention are those illustrated schematically in FIG. 1C, wherein one paratopic portion binds specifically to (immunoreacts with) an epitope expressed on a target cell surface, whereas the other paratope immunoreacts with the T3 antigen expressed on the surfaces of T cells. The paratopic portions that immunoreact with the T3 antigen are often referred to herein as anti-T3 paratopic portions or anti-T3 Mabs.

Inasmuch as the hybrids are utilized in conjunction with the before-described method, the target cell epitope bound by the bispecific hybrid paratope is different from the epitope bound by the monoclonal paratopic molecule utilized in the before-described method to avoid competition for the epitope, and provide a second means for target cell killing mediated by a monoclonal paratopic molecule. Such an epitope can be referred to as a non-interfering epitope. Non-interference of the epitope can be readily assessed by binding studies that utilize a before-described Mabs and bispecific hybrids. Exemplary bispecific hybrid molecules are discussed hereinafter.

An IL-2-activated leucocyte population such as activated PBMCs contains numerous T cells that contain the T3 antigen; i.e., T3+ cells. Such T3+ cells are useful in this aspect of the invention, but are not believed to be the activated effectors utilized in the before-mentioned method. The discussion that follows illustrates that at least three groups of activatable effector cells (effector precursors) are present in a usually found leucocyte population.

In a first embodiment of the use of bispecific hybrid molecules, lecuocytes such as PBMCs are activated by admixture, contact and maintenance (co-incubation) of those cells with an effective amount of an anti-T3 Mab under biological conditions for a period of time sufficient for the T cells to be activated. A sufficient amount of activation can be achieved when the concentration of T3+ cells in the culture is about 75 percent of that originally present, with the number of viable cells in the culture remaining about constant, or increased over those originally present. More preferably, the PBMCs are cultured until the concentration of T3+ cells is about 50 percent of that originally present, with the total number of viable cells in the population again remaining constant, or being increased over the number originally present.

A suitably activated effector cell population can typically be achieved after 3 and 5 days of co-incubation culture, respectively, using cell densities of about $3-8 \times 10^5$ cells per milliliter (ml), at about 200-600 nanograms per ml (ng/ml) of purified OKT3 (ATCC CRF 8001) as the anti-T3 Mab, and at about 37 degrees C. The relative numbers and thus concentrations of T3+ cells can readily be ascertained using a fluorescent label linked to antibodies that immunoreact with T3 such as a fluorescein isothiocyanate (FITC) conjugate of OKT3 or Leu-4 antibodies, and a fluorescence-activated cell sorter (FACS).

The activated cell population typically contains increased numbers of T cells that do not exhibit the T3 antigen (T3−), but do exhibit either the T4 or T8 antigens (T4+ or T8+). Such cells can be referred to as T3−, T4+ or T3−, T8+. [Monoclonal antibodies OKT4 (ATCC CRL 8002) and OKT8 (ATCC CRL 8014) can be utilized to identify the T cell antigens.] A similar population of activated T8+ cells is believed attainable by separate activation of a resting T8+ cell population with OKT3 or Leu-4 and IL-2.

Engagement of T3 by OKT3 has been shown, under defined experimental conditions, to lead to expression of IL-2 receptors, IL-2 production and proliferation. [Van Wauwe et al. (1980) *J. Immunol.* 124:2708–2713; Schwab et al. (1985) *J. Immunol.* 135: 1714–1718; Manger et al. (1985) *J. Immunol.* 135:3669–3673; and Tsoukas et al., *J. Immunol.* 135:1719–1723.]

Interestingly however, human PBMCs activated with OKT3 as discussed herein, washed free of those antibodies, and admixed with Mab 9.2.27 (an antibody of class IgG2a that binds to a melanoma surface antigen) and M21 melanoma target cells provided target cell lysis substantially less than that observed with bispecific hybrid molecules plus the activated cells, and about the same as that observed with hybrids plus unactivated PBMCs. Jung et al. (1986) *Proc. Natl. Acad. Sci. USA* 83:4479–4483. Since IL-2 was presumably generated under those activation conditions, the cytolytic pathway followed by the previously discussed method aspect of the invention is apparently different from that of anti-T3-activation of T cells plus hybrids.

Photomicrographs of the activated effector T cells indicate the presence relatively larger cells that possessed granular basophilic cytoplasm. Photomicrographs of unactivated cells show the typical morphology of small resting lymphocytes with a dense nucleus and scant cytoplasm. See Jung et al. (1986) *Proc. Natl. Acad. Sci. USA* 83:4479–4483.

After activation and washing to separate the anti-T3-activated cells from the anti-T3 Mab, the anti-T3-activated effector cell-containing PBMC culture is typically utilized within about 24 hours. In that use, the cells are admixed, contacted and maintained (co-incubated) with the bispecific hybrid molecules for a time period sufficient for the first anti-T3-containing paratopic portion to immunoreact with T3-containing cells present in the culture, e.g., for about 5 minutes to about one hour at 37 degrees C. to form bispecific anti-T3-armed, anti-T3-activated T effector cells.

A cytotoxic amount of those bispecific anti-T3-armed, anti-T3-activated effector T cells is thereafter dispersed in an aqueous physiologically tolerable diluent medium, as discussed before. The resulting composition is admixed with the target cells and the effector-target cell admixture is maintained for a period of time sufficient for killing of the target cells, as discussed previously.

Using armed effectors from a PBMC preparation as a standard, exemplary E:T ratios for in vitro target cell killing are similar to those discussed previously when using about $1.5 \times 10^4$ target cells per 100 microliters (ul); i.e., about $1.5 \times 10^5$ cells/ml, in a $^{51}$Cr cytolysis assay as discussed herein.

For in vivo use, it is convenient to use a single PBMC population for both aspects of the invention. Consequently, where a single preparation is so used, the cells are typically activated over a 3 to 5 day time period with anti-T3 as discussed before, as well as being activated within about 24 hours of their use with IL-2, as discussed previously. The appropriate bispecific hybrid and monoclonal paratopic molecules are admixed to coat their respective effector cells and form the two types of armed, activated effector cells. The particular order of activation and coating is not of particular import so long as both types of armed, activated effectors are present in the resulting composition, and the composition and its armed, activated effectors are substantially free of IL-2 when introduced into the recipient mammal.

The two modalities can thus be administered to their target cells in vivo or in vitro simultaneously from a single leucocyte preparation or from separate preparations that are administered substantially simultaneously; i.e., within about 15 minutes of each other. Each of the two modalities can also be administered separately, about zero hours to about 3 days apart, with either being administered first. Repeated administrations of each can also be administered.

In an alternative embodiment, a procedure similar to that reported by Perez et al. (1986) *J. Exp. Med.* 163:166–178 is utilized. Thus, a leucocyte preparation such as PBL or PBMCs is activated under biological conditions at 37 degrees C. with IL-2 for a time period of about 24 to about 36 hours. The IL-2-activated cells are then coated with bispecific hybrid molecules as described herein.

Those workers depleted their PBMC population of monocytes by passage of the PBMCs over a Sephadex G10 column following the procedures of Hathcock et al. (1981) in *Manual of Macrophage Methodology: Collection, Characterization, and Function,* Herscowitz et al. eds., Marcel Decker, Inc., N.Y., pages 723–745, and also depleted the population of Leu-11+ cells by incubation with Leu-11b (Beckin, Dickinson & Co., Mountain View, Calif.) and rabbit complement. Such depletions are not necessary herein, since both monocytes and Leu-11+ cells are useful effectors.

Perez et al. activated their depleted cell populations using 10[6] cells/ml with 10 U/ml of rIL-2 for the 24-hour activations. For longer activations, the same amount of rIL-2 was added daily. Where a Perez et al. type method is utilized as a separate administration, the activation regimen discussed by those authors can be followed. However, where a single unit dose administration of effector cells is utilized, the previously discussed IL-2 activation is followed.

Once the cells are activated, they are separated from the IL-2-containing culture medium as discussed before, and are coated with bispecific hybrid molecules. The coated, IL-2-activated effector cells are thereafter admixed, contacted and maintained with the target cells as already discussed. These coated, activated cells are preferably used within about 8 to about 24 hours of activation and can be administered in the same manner as the previously-discussed armed, anti-T3-activated effector cells.

In either of the two before-discussed embodiments utilizing hybrids, the effector cells are coated with hybrids at a ratio of about 5 micrograms of purified hybrid per about 10[8]–10[9] cells. Any unbound hybrids need not be removed from the activated, armed (coated) T effector cell-containing composition, although the cells can be rinsed to free them of (separate them from) any unbound hybrids as well as any toxic amounts of IL-2.

It is also noted that the bispecific hybrid molecules provide a cytotoxic effect when utilized with unactivated effector cells, albeit a smaller cytolytic effect is found. Thus, a cytotoxic amount of the bispecific hybrid molecules can also be administered without the step of coating them on their respective activated effector cells.

As noted previously, the bispecific hybrid molecule contains the anti-T3 paratope, as can be provided by the commercially available Mabs OKT3 and Leu-4, as well as a paratope that immunoreacts with an epitope of the target cell surface but does not interfere with and is different from the epitope on the antigen bound by the IgG1, IgG2a, IgG2b or IgG3 paratopic molecule described before. Exemplary target cell-binding Mabs useful in the bispecific hybrid molecules, in addition to the anti-T3 Mab, are listed in Table 2 along with an exemplary associate Mab used in the first-discussed method.

Because neither ADCC nor complement-dependent cytotoxicity (CDC) are required of the hybrids, paratopic portions, e.g., Fab, F(ab') F(ab') or F(ab')2 antibody portions, of IgM Mabs can also be utilized in the hybrids.

| Mab[2] | ATCC No.[3] | Antigen Bound[4] | Associate Mab[5] | Illust. Target[6] |
|---|---|---|---|---|
| Target Paratopes of Bispecific Hybrid Molecules[1] | | | | |
| MB 3.6 | HB 8890 | GD3 | 14.18 | M21 melanoma |
| 14.18 | HB 9118 | GD2 | 11 C64 | M21 melanoma |
| R24 | — | GD3 | 9.2.27 | FM9 melanoma |
| 126[7] | HB 8568 | GD2 | MB 3.6 | M14 melanoma |
| CLH 6[8] | HB 8232 | colon cancer | HT 29/26 | HT 29 colon adenocarcinoma |
| CLH 479[8] | HB 8241 | colon cancer | HT 29/26 | SW 48 colon cancer |
| 19.9[9] | CRL 8019 | CEA | HT 29/26 | SW 1222 colorectal carcinoma |
| F36/22[10] | HB 8215 | Breast carcinoma | HT 29/26 | BT-20 breast carcinoma |
| CLNH5[11] | — | Lung carcinoma | 14.18 | T293 lung carcinoma |
| T43[12] | HB 8275 | Bladder cancer gp80, 60 | T16 | T24 bladder carcinoma |
| 16-88[13] | — | Colon carcinoma | HT 29/26 | SW 403 colon carcinoma |
| B38.1[14] | — | 70 kd carcinoma protein | F 64.5 | BT-20 or MCF-7 breast cancer |
| 5 G6[15] | — | 39 kd Hib outer membrane protein | 2 E 10 | Hib |

[1]The bispecific hybrid molecules contain a first anti-T3 Mab paratope such as OKT3 that immunoreacts with the T3 antigen and a second paratope that immunoreacts with an epitope expressed on the surface of the target cells.
[2]Mab = the published name or designation of the monoclonal antibody containing the target epitope-binding paratope. Citations to Mabs MB 3.6, 14.18, R 24 and F36/22 are in the Table 1 footnotes.
[3]ATCC No. = the reported ATCC accession number of the hybridoma that secretes the indicated Mab.
[4]Antigen bound by the Mab of note 2.
[5]Associate Mab = the IgG1, IgG2a, IgG2b, or IgG3 intact monoclonal paratopic molecules utilized in the before-discussed method.
[6]Illust. Target = illustrative target cells with which the second paratopes of the hybrid molecules immunoreact and with which the associate Mabs react.
[7]Cheresh et al. (1986) J. Cell. Biol. 102:688. U.S. Pat. No. 4,675,287.
[8]U.S. Pat. No. 4,579,827.
[9]U.S. Pat. No. 4,349,528.
[10]European Patent Application No. 84400420.0, publication No. 0 118 365, published September 12, 1984.
[11]Patent application PCT/US83/00781, WO 83/04313.
[12]European Patent Application No. 84102517.4, publication No. 0 118 891, published September 19, 1984.
[13]European Patent Application No. 85300610.4, publication No. 0 151 030, published August 7, 1985.
[14]U.S. Pat. No. 4,522,918.
[15]U.S. Pat. No. 4,455,296.

Thus, in a preferred embodiment of this method aspect of the invention, a T cell population containing T3+ and T8+ cells, as found in a leucocyte preparation such as PBL and PBMCs, is activated either by culturing those cells in an aqueous medium with (a) an amount of monoclonal anti-T3 antibodies and at least for a time period sufficient to decrease the T3+ cell population by about 75 percent while maintaining or increasing the total number of cells in the culture, or (b) with an activating amount of IL-2, to form activated effector T cells.

The activated effector T cells are thereafter separated from the anti-T3 antibodies or IL-2, as by rinsing. The separated, activated T effectors are admixed and contacted in an aqueous medium with bispecific hybrid molecules containing a first paratopic portion that immunoreacts with the T3 antigen (anti-T3 Mab) and a second paratopic portion that immunoreacts with an epitope expressed on the surface of a target cell. The admixed and contacted activated effector T cells and hybrids are maintained under biological conditions for a time period sufficient to bind the hybrids to the activated effector T cells (coat the activated effector cells) and form bispecific hybrid-armed (anti-T3), activated effector T cells. Those armed cells are then typically separated as by rinsing from the medium, and are collected.

The bispecific hybrid-armed, activated effector T cells are dispersed in an aqueous physiologically tolerable diluent medium, and an amount of the resulting composition containing a cytotoxic amount of these armed, activated T cells is thereafter admixed and contacted with target cells. That contact is maintained under biological conditions for a time period sufficient for target cell killing to take place, as discussed before.

The T cell population can be a pre-sorted population as can be obtained by FACS. More preferably, the T cell population to be activated is present in the leucocyte population utilized in the before-discussed method. Thus, the IL-2-activatable Leu-11+ effectors that contain IgG1, IgG2a, IgG2b or IgG3 Fc Mab receptors and the anti-T3- or IL-2-activatable T3+,T8+ T cell effectors are portions of the same leucocyte population.

In an exemplary procedure using M21 melanoma cells that express both disialogangliosides GD2 and GD3 on their surfaces as target cells, a leucocyte preparation such as PBMCs is activated under biological conditions using OKT3 as the anti-T3 Mab for a time period of 5 days, using $8 \times 10^5$ PBMCs per ml, OKT3 at 600 ng/ml and DMEM as the aqueous medium. The activated cells are thereafter separated from the OKT3 by washing.

The separated anti-T3 activated cells are then resuspended in an aqueous medium at about $1 \times 10^6$ cells/ml, and rIL-2 at about 500 U/ml is admixed. The resulting cell suspension is maintained for 4 hours under biological conditions at 37 degrees C. to form an IL-2-activated cell population. The resulting cells containing both anti-T3-activated T effector cells and IL-2-activated effectors is separated from the rIL-2, as by washing. (The anti-T3 Mabs can also be separated from the activated cells at this separation.)

The separated, activated effector cell-containing preparation is then co-incubated with an anti-GD2 Mab such as Mab 14.18 secreted by the hybridoma having ATCC accession number HB 9118 at about 200 ug/ml and with bispecific hybrid molecules whose first paratopic portion is that of OKT3 (ATCC CRL 8001) and whose second paratopic portion is that of the anti-GD3 Mab MB 3.6 (ATCC HB 8890) to form an aqueous composition containing coated, armed, activated effector cells. An effective amount of that composition that contains cytotoxic amounts of armed, rIL-2 activated effectors and armed, anti-T3-activated effectors is then co-incubated with the M21 melanoma target cells for a time period such as 4 hours sufficient for lysis of the target cells.

II. RESULTS

The specific results discussed hereinafter illustrate that a relatively brief ex vivo co-incubation of human rIL-2 with leucocytes such as human peripheral blood mononuclear effector cells potently augments both natural killing and ADCC-mediated cytolysis of human melanoma and neuroblastoma cells in vitro, and of human melanomas in vivo. The IL-2-activated effector cells can be considered to be lymphokine-activated killer (LAK) cells, although the PBMCs utilized were not incubated for the prolonged time periods described by others [Yron et al. (1980) *J. Immunol.* 125:238–245; Lotze et al. (1981) *Cancer Res.* 4:4420–4425; Grimm et al. (1982) *J. Exp. Med.* 155:1823–1841; Grimm et al. (1983) *J. Exp. Med.* 158:1356–1361]. Alternatively, these effector cells could be regarded as activated natural killer (NK) cells, since such cells are effective in ADCC.

The results presented here were obtained with PBMC's from twenty different donors that were analyzed in over sixty independent ADCC assays. In all cases examined, the results clearly and uniformly demonstrated that ex vivo activation of human PBMCs with a relatively low dose and brief exposure of the human PBMCs to rIL-2 augments both natural killing and ADCC-mediated cytolysis of human melanoma and neuroblastoma target cells.

Those results also showed that Mabs 14.18 (anti-GD2), and 11C64 (anti-GD3) effectively "armed" effector cells to specifically direct those cells to their respective targets, either with or without rIL-2-induced activation. Additionally, the same ex vivo protocol employing rIL-2 that augments natural killing and ADCC with PBMCs from normal donors was also effective with PBMCs obtained from melanoma patients. It is noteworthy that a similar level of cytolytic augmentation of PBMCs was induced by rIL-2 over a dose range of 3 logs, suggesting that once a threshold level of activation is achieved, it is not further enhanced by additional rIL-2.

It is also noted that a wide range of ADCC activity was observed for PBMCs among the twenty donors, whereas the relative level of ADCC activity of an individual donor's PBMCs repeatedly exhibited a reproducible pattern. In some cases, a clear synergism was observed whenever the combined modality of ex vivo rIL-2 activation and effector-targeting Mab was employed. In other cases, particularly in vitro, the rIL-2-induced augmentation appeared more like an additive effect of combining the net cytolysis of rIL-2-induced natural killing with independently generated killing by ADCC in the absence of rIL-2. In either event, use of ex vivo rIL-2 activation was shown to be efficacious and thereby its use in vivo can avoid the toxicity that accompanies systemic treatments with rIL-2.

The duration of lytic activation maintained in the absence of rIL-2 can also vary among individual donors. However, activation data obtained with rIL-2-activated PBMCs suggest that once the effector cells of some donors useful in the ADCC killing method (the IgG1, IgG2a, IgG2b or IgG3 Fc receptor-containing, IL-2-activated effectors) are activated and then depleted of rIL-2, they continue to develop and increase their activated state.

The results further suggest the existence of varying levels of cellular lytic activation within the population of normal human donors. This also appears to be the case for potential levels of lytic activation achieved by lymphokine-induced augmentation. This variability in lytic potential also was suggested by previous observations with murine effector cells that are considerably less responsive in ADCC than human effector cells [Honsik et al. (1985) *Natural Immunity and Biological Response* 4:253]. In addition, short-term co-incubation (4-hour) of murine effector cells with rIL-2 does not significantly increase their ability to lyse human melanoma cells.

Irrespective of variations in killing capacity of PBMCs from different human donors, the cytolytic activity of such cells obtained from either normal individuals or melanoma patients can be consistently and reproducibly augmented by a brief ex vivo co-incubation with relatively low doses of rIL-2. These results agree with those reported by Svedersky et al. (1984) *J. Immol.* 133:714–718 who demonstrated that a brief (5 minute) exposure of human PBMCs to rIL-2 can augment natural killing on human A549 and K562 erythroleukemia targets.

A. The Melanoma-Associated Disialoganglioside GD3 Provides a Relevant Target Antigen In Vivo Studies were initiated in the xenotransplant nude mouse model to determine whether GD3 can effectively be used as a target structure for immunotherapy. A subcutaneous injection of $2.5 \times 10^6$ M14 human melanoma cells was made into the right and left flanks of athymic (nu/nu) BALB/c mice. In a separate study using A375-P human melanoma cells, $5 \times 10^6$ cells were injected subcutaneously into the right flanks of such animals.

Therapy was provided on days 2, 4, 9, 11, 14, 16, 21, and 23 after the initial melanoma transplant with the animals receiving an intravenous injection of either PBS or 75 micrograms (ug) of Mab MB3.6 (anti-GD3) in PBS as an aqueous physiolgically tolerable diluent medium. The above therapy protocol was successful in suppressing tumor establishment for up to 40 days after inoculation of M14 melanoma cells, 99 percent of which reacted with Mab anti-GD3 by FACS analysis. However, this treatment was ineffective when applied on A375-P melanoma cells since only 13 percent of them reacted with anti-GD3 Mabs.

In addition, the suppression of growth in the case of the M14 xenotransplant was found to be transient since tumors developed in 50 percent of the animals by day 70. Such tumors were re-established in tissue culture and subsequently underwent FACS analysis for GD3 expression.

Approximately 95 percent of cells from all these reestablished tumors expressed GD3; however, cells from 5 out of 6 tumors exhibited a marked reduction (50 percent) in the mean intensity of fluorescence (MIF); i.e., a 50 percent decrease in density of GD3 when compared to the parental M14 cell line maintained in tissue culture. In contrast, the expression of HLA Class I antigens and melanoma-associated proteoglycans remained similar to that of the parental M14 cell line with only minor variations being observed in the expression of Class II HLA antigens.

Thus, the continued growth of these melanoma tumors in athymic (nu/nu) mice treated with Mab MB3.6 is not caused by immunoselection of a GD3-negative variant but is rather due to a variant that expresses lower levels of this disialoganglioside. Such tumor cells may even temporarily modulate GD3, with some cells escaping therapy, possibly because therapy time and amount of antibody injected may have been insufficient. These results prompted several initial in vitro studies using anti-GD3 Mabs in conjunction with effector cells as an alternative to Mab therapy alone.

B. Effector Cells with NK Activity Armed with Anti-GD3 Exert a Prominent Effect in ADCC Cells with NK activity armed with Mab MB3.6 markedly increased ADCC against human melanoma tumor cell targets, supporting the interpretation of previously reported effects on tumor suppression in vivo achieved by such effector cells in conjunction with Mab 9.2.27 (IgG2a) directed against a melanoma-associated proteoglycan [Schulz et al. (1985) *J. Exp. Med.*, 161:1315–1325]. It was then determined whether cells with NK activity also were the major effector cell population responsible for the increase in ADCC when Mab MB3.6 (anti-GD3) was used together with mouse mononuclear splenocytes against human melanoma target cells. The use of splenocytes from NK-deficient C57BL/6bgJ/bg/J mice abrogated the positive ADCC observed with splenocytes from NK-competent C57 BL/6 or NIH (nu/nu) mice. Thus, cells with NK activity appear to be the major effector cell population in these studies.

It was reported that human mononuclear cells obtained from either normal donors or recently resected melanoma patients effectively mediated ADCC against M21 melanoma cells [Cheresh et al. (1985) *Proc. Natl. Acad. Sci. USA* 82:5155–5159]. Results of ongoing studies with human PBLs, fractionated on a discontinuous Percoll gradient to provide an enriched population of NK cells, demonstrate a clear enhancement in ADCC activity in fractions containing greater than 50 percent of the NK-rich large granular lymphocytes (LGL) that exhibited Leu-11 positivity (Leu-11+) in fluorescence-activated cell sorter (FACS) analysis. In those studies, the LGL-enriched fractions produced a specific lysis of greater than 80 percent with an effector to target ratio as low as 6:1 as compared to mononuclear PBLs that generated a maximum specific lysis of only 65 percent at effector to target ratios as high as 200:1.

The results of studies employing effector cells obtained from NK-deficient and NK-competent mice combined with the data obtained with human PBLs enriched for LGLs with high NK activity, suggest a pivotal role for such cells in antibody-directed cellular cytotoxicity events mediated by anti-GD3 Mabs of the IgG3 subclass. The encouraging ADCC results obtained when utilizing the anti-disialoganglioside Mabs prompted further in vitro as well as in vivo evaluation of such a therapeutic protocol by employing "armed" activated and unactivated effector cells directed by such antibodies.

C. Monoclonal Antibodies to Gangliosides GD2 and GD3 Evoke Specific Cell-Mediated Lsis With or Without rIL-2 Activation The melanoma cell line M21 that expresses both disialogangliosides GD2 and GD3, and the neuroblastoma cell line SK-N-AS, which is GD2 positive and GD3 negative, were each labeled with $^{51}Cr$, and used as target cells. Three Mabs of the IgG3 subclass were used to target human PBMCs; i.e., 11C64 (anti-GD3), 14.18 (anti-GD2) and J606 (anti-levan and inulin). As shown in Table 3, below, the effector cells armed with Mabs directed against GD3 and GD2 exhibited exquisite specifically for their respective targets, whereas cells armed with the control Mab J606 were non-reactive.

Addition of rIL-28 500 units per milliliter (U/ml)] to the target-effector admixture did not create a non-specific enhancement by these armed effector cell populations. Background lysis induced by incubation of rIL-2 with target cells alone was routinely less than about 2 percent.

TABLE 3

Specificity of Anti-GD2 and GD3-Directed
Cell-Mediated Killing of Human Melanoma
and Neuroblastoma Cells[1]

| PMBC + Treatment[4] | M21 Melanoma Targets[2] | | | SK—N—AS Neuroblastoma Targets[3] | | |
|---|---|---|---|---|---|---|
| | Percent Specific Lysis at E:T Ratios: | | | | | |
| | 100 | 50 | 25 | 100 | 50 | 25 |
| rIL-2 | 24 | 16 | 7 | 19 | 9 | 7 |
| Mab 11C64 | 40 | 21 | 7 | 4 | 0 | 0 |
| Mab 11C64 + rIL-2 | 67 | 54 | 28 | 14 | 9 | 4 |
| Mab 14.18 | 47 | 19 | 7 | 29 | 8 | 4 |
| Mab 14.18 + rIL-2 | 66 | 42 | 20 | 46 | 25 | 13 |
| Mab J606 | 3 | 4 | 3 | 3 | 1 | 1 |
| Mab J606 + rIL-2 | 24 | 16 | 7 | 19 | 9 | 3 |

[1]ADCC mediated by Mabs 11C64 (anti-GD3) and 14.18 (anti-GD2) and normal human effector cells on human melanoma and neuroblastoma target cells at the effector to target cell ratios (E:T) shown. The percentage of specific lysis was determined on $^{51}$Cr-labeled targets in the presence or absence of rIL-2 during a 4 hour assay. Mab J606 does not bind to either target cell line.
[2]M21 melanoma cells express GD2 and GD3.
[3]SK—N—AS cells express GD2 only.
[4]In each case, the concentration of monoclonal antibody was 25 ug/ml, the amount of rIL-2 500 U/ml, and the number of target cells was $5 \times 10^5$/ml.

D. NK and ADCC Cytolytic Activity are Enhanced by Low Doses of rIL-2

In order to analyze the potentiation of lytic activity of PBMCs of two independent donors, rIL-2 was added to the 4-hour ADCC assay at doses ranging from 50 U/ml to 50,000 U/ml. A minimum dose of 50 U/ml was selected since lower concentrations of rIL-2 proved ineffective on PBMCs.

From these donors, an almost identical degree of enhancement in lytic activitiy was observed over a 3 log range when rIL-2 ranging from 50 U/ml to 50,000 U/ml were added to the ADCC assay in combination with 25 ug/ml of Mab 11C64. These data are shown in Table 4.

TABLE 4

Effect of Increasing Concentrations of
rIL-2 on Natural Killing and ADCC Activity[1]

| Effector:Target | rIL-2 in U/ml | | | | | |
|---|---|---|---|---|---|---|
| | 50 | 250 | 2500 | 5000 | 20,000 | 50,000 |
| | Natural Killing (% Specific Lysis)[2] | | | | | |
| 50:1 | 10 | 12 | 11 | 10 | 12 | 13 |
| 25:1 | 5 | 8 | 4 | 5 | 5 | 7 |
| 6:1 | 1 | 3 | 0 | 3 | 2 | 4 |
| | ADCC (% Specific Lysis)[3] | | | | | |
| 50:1 | 58 | 56 | 59 | 52 | 58 | 57 |
| 25:1 | 38 | 42 | 35 | 35 | 40 | 39 |
| 6:1 | 19 | 19 | 18 | 17 | 19 | 16 |

[1]M21 human melanoma cells were labeled with $^{51}$Cr and challenged with human peripheral blood mononuclear cells either in the presence or absence of Mab 11C64. rIL-2 was added to a 4-hour assay over a 3 log concentration, and the percentage of specific lysis was determined for PBMCs receiving rIL-2 and/or Mab.
[2]Natural killing achieved with PBMCs in the absence of rIL-2 ranged from 3–5%.
[3]Specific lysis caused by admixture of Mab 11C64, rIL-2 and PBMCs.

In the case of donor 1, at an effector to target cell (E:T) ratio of 25:1, the increase in NK lysis induced by rIL-2 ranged from 4 percent to 8 percent. Lysis obtained by unactivated PBMCs armed with Mab 11C64 was 16 percent, whereas the combined modality (PBMCs+rIL-2 +Mab 11C64) produced lytic values ranging from 35 percent to 42 percent. These results are noteworthy since the combined modality produced a net mean lysis of 38 percent; i.e., approximately a 100 percent increase over armed effector cells without rIL-2. This synergism for donor 1 was repeated in two additional studies. In this same study, donor 2 exhibited cytolytic reactivity over the 3 log range of rIL-2 concentrations similar to those levels observed for donor 1.

E. Cytolytic Enhancement of Human Mononuclear Cells by rIL-2

ADCC studies indicated that at a relatively high E:T ratio of 100:1, ex vivo co-incubation of PBMCs and rIL-2 for either 15 minutes or 4 hours resulted in comparable levels of Mab-directed killing in the ADCC assay of 95.5 percent and 93.4 percent, respectively. Mab 11C64-directed killing in the absence of activation with rIL-2 was 75 percent (FIG. 2).

Examination of this cytolytic enhancement at a lower E:T ratio of 25:1 again revealed that lytic activation occurs rapidly. Specifically, ADCC lytic activity increased from 24 percent to 44 percent in 30 minutes and continued to rise throughout the duration of the 4-hour co-incubation up to 64 percent. In separate studies, a cytolytic augmentation induced by rIL-2 activation was observed after a 10-minute co-incubation with mononuclear effector cells.

F. Natural Killing and Mab-Directed Killing of Human Melanoma Target Cells are Augmented by rIL-2 Activation These studies determined that a brief co-incubation of rIL-2 (250 U/ml) with human peripheral blood mononuclear cells (PBMCs) can enhance ADCC against melanoma target cells. Here, such effector cells were obtained from 3 normal donors and the following five groups were assessed for lytic activity on $^{51}$Cr-labeled M21 target cells in a 4-hour assay: (a) rIL-2 alone; (b) PBMCs alone; (c) PBMCs plus 25 ug/ml Mab 11C64; (d) PBMCs plus 250 U/ml rIL-2; and (e) the combined modality of PBMCs plus 25 ug/ml Mab 11C64 plus 250 U/ml rIL-2.

Figure 4:
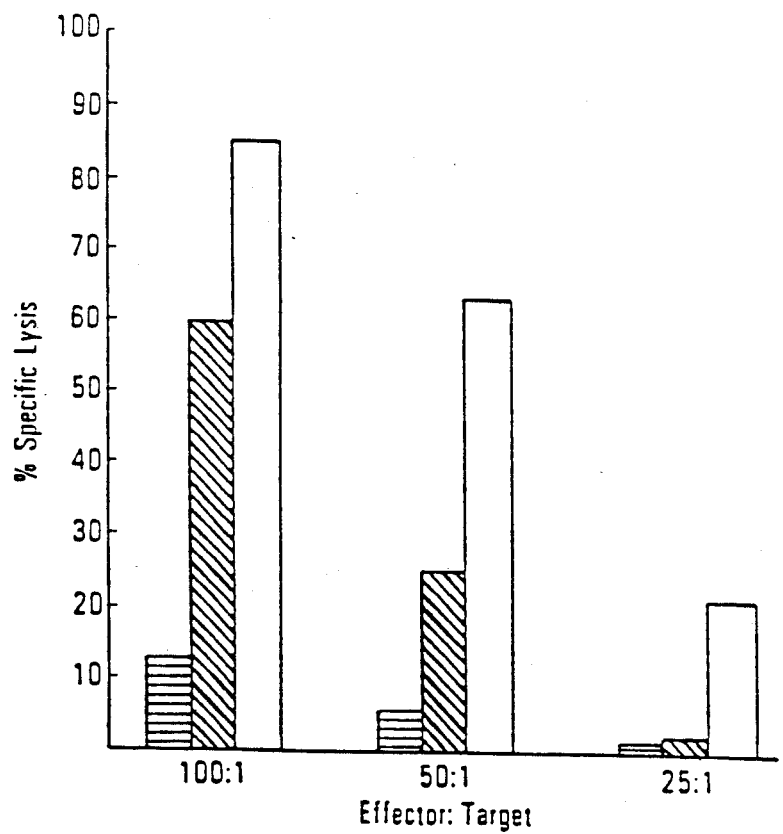
FIG. 4 is another set of bar graphs that illustrate augmentation of ADCC by IL-2-activated human PBMCs. Here, PBMCs from a normal, asymptomatic human donor were admixed with target human $^{51}$Cr-labeled M21 melanoma cells at different effector to target cell ratios, as shown. The PBMC treatments during the 4-hour assay illustrated included: admixture with 250 U/ml of rIL-2 (horizontally-hatched bars); admixture with Mab 11C64 at 25 micrograms per milliliter (ug/ml) (diagonally-hatched bars); and co-incubation with 250 U/ml of rIL-2 plus 25 ug/ml Mab 11C64

A clear enhancement in lysis was observed with the cells of all three donors whenever PBMCs were co-incubated with rIL-2 and armed Mab 11C64 as compared to either PBMCs alone or PBMCs incubated with antibody or activated with rIL-2. Representative results obtained with one donor's effector cells are presented in FIG. 4. Background lysis induced by incubation of rIL-2 with target cells alone was less than about 2 percent.

G. Cytolytic Augmentation Induced by Ex Vivo rIL-2 Activation is Maintained in its Absence A 4-hour ex vivo co-incubation of PBMCs with rIL-2 induced a marked increase in lytic acitivity both in NK-mediated lysis and Mab-directed lysis (ADCC) that is maintained for at least 20 hours in the absence of rIL-2 (Table 5). In the following studies, PBMCs were co-incubated ex vivo for 4 hours with rIL-2 (500 U/ml), thoroughly washed free of rIL-2, and maintained for an additional 20 hours in the absence of rIL-2 in DMEM plus 10 percent fetal calf serum (FCS) at 37 degrees C. in a 7.5 percent $CO_2$ humidified atmosphere. The lytic activity was then assessed in the ADCC assay by comparing the respective efficacies of the same donor's PBMCs co-incubated under similar conditions for 24 hours, without rIL-2 activation, or of fresh PBMCs obtained th day of the assay from the same donor. These results are shown in Table 5, below.

TABLE 5

Enhancement of ADCC Cytolytic Activity by Pretreatment of PBMCs with rIL-2[1]

| Treatment[2] | Percent Lyses at E:T Ratios of: | | |
|---|---|---|---|
| | 100:1 | 50:1 | 25:1 |
| A | 56 (3)[3] | 31 (3) | 14 (2) |
| B | 65 (13) | 47 (7) | 27 (4) |
| C | 83 (77) | 70 (58) | 52 (23) |
| D | 80 (76) | 80 (52) | 60 (23) |

[1]The cytolytic activity was assessed on $^{51}$Cr-labeled M21 human melanoma cells in quadruplicate wells using the effector to target cell ratios (E:T) shown. The standard deviation in cpm measurements did not exceed 5%.
[2]Treatment of PBMCs ($5 \times 10^5$ cells/ml) was as follows: (A) fresh PBMCs; (B) PBMCs maintained for 24 hour at 37 degrees C.; (C) PBMCs pretreated with 500 U/ml rIL-2 for 4 hours, washed and maintained for 20 hours at 37 degrees C. in the absence of rIL-2; and (D) PBMCs maintained in the presence of 500 U/ml for 24 hours at 37 degrees C. All treatments included 200 ug/ml of Mab 11C64.
[3]Figures in parentheses denote percent lysis obtained in the absence of Mab 11C64.

The data of Table 5, above, reveal that a 4-hour ex vivo activation of PBMCs with rIL-2 (500 U/ml) followed by the removal of rIL-2 for 20 hours resulted in augmented lytic activity, (NK lysis of 77 percent; Mab 11C64-directed killing 82.7 percent). This lytic augmentation was maintained and was comparable to that generated by PBMCs continuously exposed to rIL-2 activation for 24 hours (NK lysis of 76 percent; Mab 11C64-directed killing 80 percent). The control values obtained for the overnight co-incubations were NK lysis of 13 percent and 64.6 percent for Mab 11C64-directed killing, respectively.

H. The Cytolytic Activity of Melanoma Patients' Mononuclear Cells is Enhanced by a Brief Ex Vivo Co-incubation with rIL-2

PBMCs were obtained from four melanoma patients that differed in their stage of disease; i.e., showed markedly different tumor loads. At an E:T ratio of 100:1, melanoma patients' PBMCs plus Mab 11C64 induced lysis ranging from 24 percent to 73 percent. When melanoma patients' PBMCs were incubated with rIL-2 for the duration of the 4 hour assay, the induced lysis ranged from 18-39 percent. Finally, co-incubation of melanoma patients' PBMCs with rIL-2 and Mab 11C64 induced lysis that ranged from 48-88 percent. In these same studies, normal control values were 30 percent for Mab 11C64-directed PBMCs, 25 percent for PBMCs plus rIL-2, and 54 percent lysis for the combined modality.

Figure 3:
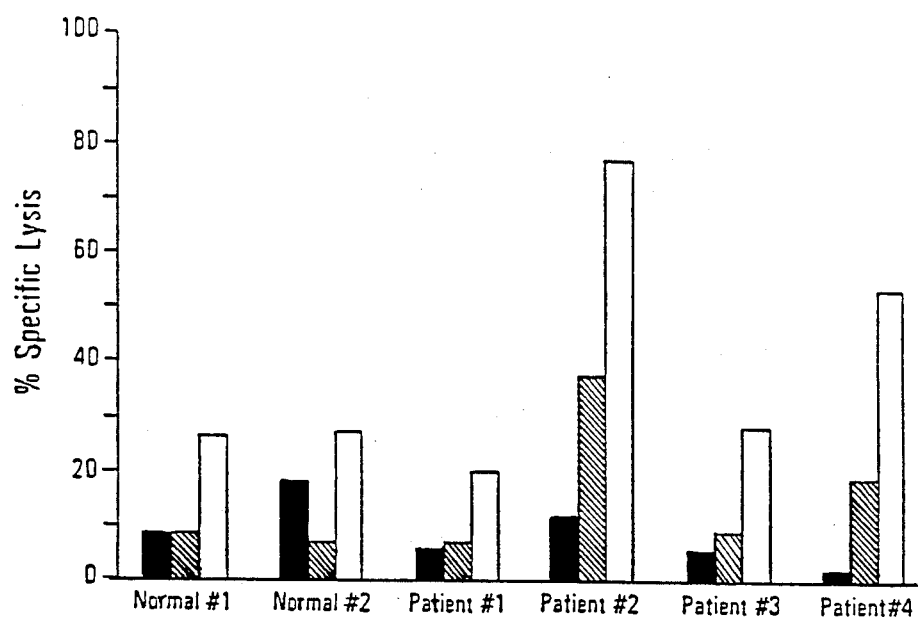
FIG. 3 is a bar graph showing cytolysis by ADCC of $^{51}$Cr-labeled M21 human melanoma cells challenged with PBMCs from four melanoma patients and two normal, asymptomatic persons used as controls, using a 4-hour assay time. Patients 1, 2 and 4 were in remission whereas patient 3 had advanced disease and a large tumor burden. An effector to target cell ratio of 50:1 was utilized with the following effector co-incubations prior to effector-target admixture: 500 U/ml rIL-2 (closed bars); 25 micrograms per milliliter (ug/ml) Mab 11C64 (hatched bars); and 500 U/ml rIL-2 plus 25 ug/ml Mab 11C64 (open bars).

All four patients' PBMCs showed a distinct enhancement in percent lysis whenever the combined modality of co-incubation of PBMCs with rIL-2 and Mab 11C64 arming was applied (FIG. 3). It is of considerable interest that PBMCs from patients, with widely differing tumor burdens, proved effective in ADCC when "armed" with Mab 11C64 and activated ex vivo with rIL-2.

I. Mab Armed Human PBMCs Activated Ex Vivo with rIL-2 Suppress Human Melanoma Tumor Growth in Athymic (nu/nu) Mice Subcutaneous injection of $5 \times 10^6$ M21 cells into the right flanks of athymic (nu/nu) mice resulted in the outgrowth of melanoma lesions. On day 12 after the injections, when the melanoma lesions had an average volume of 40 mm$^3$, four animals per group received the following treatment regimens: (a) PBMCs ($2 \times 10^7$) i.p.; (b) PBMCs ($2 \times 10^7$) preincubated with 400 ug of Mab 11C64 i.p.; (c) PBMCs ($2 \times 10^7$) preincubated for 4 hours with 2000 U of rIL-2; (d) PBMCs ($2 \times 10^7$) preincubated for 4 hours with 2000 U of rIL-2, washed once and subsequently armed with 400 ug of Mab 11C64 and injected i.p. in an aqueous medium; (e) control animals received PBS i.v. injections. PBMCs were armed by incubation with Mab 11C64 at 2 milligrams per milliliter in a 200 microliter volume for 30 minutes at 37 degrees C. prior to injection. The mean tumor volume (MTV) of each animal was obtained 4 weeks later by measuring the melanoma lesion with graduated calipers and using the formula:

$$MTV = \pi(d_1)(d_2)(d_3)/2.$$

All animals in the group receiving the combined modality therapy of PBMCs activated ex vivo with rIL-2 followed by arming with Mab 11C64 and subsequent injection as a cytotoxic composition showed a marked decrease in tumor volume, and one of those mice was completely tumor-free. In fact, the reduction in MTV of these animals averaged greater than 80 percent. The results of these studies are shown in Table 6, below.

TABLE 6

Effect of Anti-GD3 Mab-Armed Human PBMCs Augmented by Ex Vivo rIL-2 Activation on Human Melanoma Tumor Growth in Athymic Mice[1]

| Treatment | Mean Tumor Size (mm$^3$) |
|---|---|
| Control ($2 \times 10^7$ PBMCs) | 1452 ± 350 |
| PBMCs + Mab ($2 \times 10^7$ + 400 ug Mab) | 1330 ± 280 |
| PBMCs + rIL-2 ($2 \times 10^7$ + 2000 U) | 1208 ± 222 |
| PBMCs + Mab 11C64 + rIL-2 ($2 \times 10^7$ + 400 ug + 2000 U) | 194 ± 38[2] |

[1]M21 human melanoma cells ($5 \times 10^6$) were injected subcutaneously into 20 nude mice. Animals (4) received i.p. injections of either 200 ul of PBS or $2 \times 10^7$ PBMCs when the melanoma lesions had a MTV of 40 mm$^3$. Those PBMCs activated with rIL-2 received 2000 U for 4 hours in DMEM at 37 degrees C. with one wash prior to injection.
[2]One animal was tumor-free and the others had tumor volumes of 168, 189, and 225 mm$^3$, respectively.

J. Efficiency of ADCC-Mediated Killing of Tumor Cells by Different Monoclonal Isotypes Depends Upon the PBMC Donor Studies were carried out to evaluate whether a preference existed for a particular Mab isotype in ADCC-killing of tumor target cells. A group of isotype switch variants of the anti-GD2 Mab 14.18 were prepared using the fluorescence-activated cell sorting techniques described by Kipps et al. (1985) *J. Exp. Med.* 161:1-17. Those variants were thereafter screened in a 4-hour ADCC assay comparing the effects obtained using PBMCs from two human donors.

As can be seen from the data of Table 7, below, all of the isotypes exhibited ADCC-mediated killing activity that was above the NK activity of the donor PBMCs. Those data also show that ADCC-mediated killing by the IgG1 isotype was less than that exhibited for IgG2a, IgG2b or IgG3.

Variability between individual donors was also found that depended both upon the isotype and the target cells utilized. Therefore, although any of the four istoypes can be utilized to arm the effector cells, the optimum isotype may depend upon the donor's activatable leucocytes and the target cells.

TABLE 7
ADCC-Mediated Killing of Neuroectodermal Tumor Cell by One Anti-GD2 Mab With Differing Isotopes[1]

| | Percent of Neuroectodermal Tumor Cells Killed | | | | | |
|---|---|---|---|---|---|---|
| | M21 Donor | | T293 Donor | | SK—N—AS Donor | |
| Type of Killing[2] | 1 | 2 | 1 | 2 | 1 | 2 |
| NK | 1 | 2 | 1 | 2 | 1 | 2 |
| NK Mab 14.18 | 6 | 6 | 0 | 8 | 0 | 1 |
| IgG3 | 22 | 37 | 17 | 23 | 9 | 15 |
| IgG2a | 32 | 55 | 36 | 41 | 41 | 35 |
| IgG2b | 19 | 38 | 17 | 23 | 36 | 23 |
| IgG1 | 19 | 5 | 7 | 3 | 35 | 15 |

[1] Lysis percentages were obtained using the standard ADCC assay with $^{51}$Cr-labeled target cells as discussed in the Materials and Methods Section.
[2] Two sets of data were obtained for NK killing, whereas only one set was taken for killing by the various isotype switch variants of Mab 14.18.

III. Materials and Methods

A. Animals

BALB/c athymic nu/nu mice were obtained from the nude mouse colony at the University of California, San Diego, Calif. C57BL/6bgJ/bg/J, C57 BL/6 and NIH nu/nu mice were obtained from the Vivarium at the Scripps Clinic and Research Foundation, La Jolla, Calif.).

B. Cell Lines

The M14 and M21 human melanoma cell lines were kindly provided by Dr. D. L. Morton (University of California, Los Angeles). The SK-N-AS cell line was a gift from Dr. L. Helson, (Memorial Sloan-Kettering Cancer Center, N.Y.). The A375-P cell line is a subclone of line A-375 (ATCC CRL 1619), and was obtained from Dr. J. Fidler (University of Texas Health Sciences Center, Houston). The T293 human small cell lung carcinoma cell line was provided by Drs. Masie and Sato (University of California, San Diego). The tumor cells were maintained in RPMI 1640 medium (GIBCO Laboratories, Grand Island, N.Y.) or Dulbecco's modified Eagles's medium (DMEM; Flow Laboratories, Hamden, Conn.), each supplemented with 10 percent fetal calf serum, 1 percent glutamine, and gentamycin at 50 ug/ml (growth medium) at 37 degrees C. in 7.5 percent $CO_2$/92.5 percent air.

C. Monoclonal Antibodies

Mabs 14.18 (IgG3) (ATCC HB 9118), as well as MB 3.6 (IgG3) (ATCC HB 8890) and 11C64 (IgG3) directed against disialoganglioside GD2 and GD3, respectively, were produced in our laboratory, J606 (IgG3), anti-levan and inulin was kindly provided by Dr. M. Cohn (Salk Institute, La Jolla, Calif.). These Mabs were purified by salting out and affinity chromatography using Protein-A Sepharose (Pharmacia Fine Chemicals, Uppsala, Sweden) following the procedures of Ey et al. (1978) *Immunochemistry* 15:429–436. The collected fractions were extensively dialyzed against a 0.1 M citrate buffer at pH 6.7, containing 5 percent sucrose (w/v). The purified Mabs were stored at −70 degrees C., and their activity was assessed with an ELISA assay previously described by Cheresh et al. (1984) *Proc. Natl. Acad. Sci., USA* 81:5767–5771. The purity and stability of the Mab preparations was evident from sedimentation-velocity analysis performed with a Beckman Model E ultracentrifuge that revealed a monomeric 7S protein [Ziccardi et al. (1984) *J. Biol. Chem.* 259:13674–13679]. Hybridomas producing monoclonal antibodies 126, MB3.6 and 14.18 were deposited under the Budapest Treaty with the American Type Tissue Collection, 12301 Park Lawn Drive, Rockville, Md., and assigned the designations ATCC HB 8568, ATCC HB 8890 and ATCC HB 9118 respectively.

Isotypes were determined by ELISA as follows: Fifty microliter volumes (1:1000 dilutions in PBS) of rabbit anti-mouse IgG1, IgG2a, IgG2b, IgG3 or IgM (Southern Biotech Associates, Birmingham, Ala.) were plated per well of a flat-bottom polyvinyl chloride microtiter plate (Dynatech, Alexandria, Va.) The plates were then incubated overnight at 37 degrees C. in a drying oven. The dried plates were stored at 4 degrees C. until use. Prior to the ELISA assay, dried plates were rehydrated by two washes of two minutes each with 10 millimolar (mM) PBS, pH 7.4, containing 0.1 percent polyoxyethylene (20) sorbitan monolaurate (Tween 20) and 0.02 percent Thimerosal (sodium ethylmercurithiosalicylate; Sigma, St. Louis, Mo.).

Hybridoma culture supernatants diluted 1:2 in PBS were then added at fifty microliters per well and maintained at 4 degrees C. for 1 hour. After 2 washes, fifty microliters (ul) of horseradish peroxidase-labeled goat anti-mouse immunoglobulin (Biorad Laboratories, Richmond, Calif.) diluted 1:1000 were added to each well and maintained at 4 degrees C. for 1 hour.

The substrate used to assay bound peroxidase activities activity was prepared just prior to use and consisted of 400 micrograms/ml o-phenylenediamine (Sigma, St. Louis, Mo.) in 80 mM citrate-phosphate buffer, pH 6.0, containing 0.23 percent $H_2O_2$. After two final washes, 50 ul of substrate solution were added to each well and color was allowed to develop for 15 minutes in the dark. Color development was stopped by adding 25 ul of 4 molar (M) $H_2SO_4$ to each well, and the optical density at 492 nanometers (nm) was measured with a Multiskan ELISA Plate reader (Bio-Tek Instruments Inc., Burlington, Va.).

Isotype switch variants of IgG1, IgG2a and IgG2b isotypes were prepared in this laboratory from Mab 14.18 (IgG3) using the fluorenscence-activated 15 cell sorting method of Kipps et al. (1985) *J. Exp. Med.* 161:1–17, which disclosure is incorporated herein by reference.

Mabs OKT3, OKT4 and OKT8 are available from Ortho Diagnostic Systems of Raritan, N.J. Mabs Leu-4, Leu-11a and Leu-11b are available from Beckton Dickinson Monoclonal Center, Inc. Mountain View, Calif.

D. Antibody-Dependent Cellular Cytoxicity (ADCC)

Melanoma and neuroblastoma cells ($10^6$) were labeled in 1 ml of the before-described growth medium containing 200 microCuries (uCi) of $^{51}$Cr [sodium chromate at 1 milliCurie/ml (mCi/ml), New England Nuclear, Boston, Mass.], and were incubated for 90 minutes at 37 degrees C. The cells were then washed twice with phosphate-buffered saline (PBS; pH 7.2), and were resuspended in 2 ml of growth medium.

Target cells ($5 \times 10^3$ in 10 ul) were added to individual wells of a 96-well microtiter plate (Flow Laboratories). Purified antibody, diluted in growth medium to 200 ug/ml (25 ul), was added to wells containing the target cells. Human recombinant IL-2 (Lot #LP-303B) (a generous gift of Cetus Corporation, Emeryville, Calif.)

was prepared in *E. coli* according to Wang et al. (1984) *Science* 224:1431-1433.

Human peripheral blood mononuclear were isolated by Ficoll/Hypaque (Lymphoprep, Nygaard & Co., Oslo, Norway) gradient centrifugation from heparinized blood of either melanoma patients (generously provided by Dr. F. Meyskens, University of Arizona, Tucson) or healthy control individuals as described in Boyum (1976) in *Lymphocytes, Isolation, Fractionation, and Characterization*, eds. Nativig. These cells were added to microtiter wells at the indicated target:effector cell ratios. The plates were co-incubated for 4 hours at 37 degrees C. and processed as described previously by Cheresh et al. (1985) *Proc. Natl. Acad. Sci., USA* 82:5155-5159. The percent lysis was calculated by the formula:

$$\frac{(\text{Measured release}) - (\text{Spontaneous release}) \times 100}{(\text{Maximal release}) - (\text{Spontaneous release})}$$

Where "Measured release" is the counts per minute (cpm) of $^{51}$Cr decay measured in each study, "Spontaneous release" is the background decay; and "Maximal release" is the maximal number of counts available to be counted in the sample.

To calculate specific lysis attributable to ADCC or rIL-2 induced augmentation, the percentage lysis due to effector cells in the absence of antibody or rIL-2; i.e., natural killer (NK) lysis, was subtracted from each value obtained above.

The present invention has been described with respect to preferred embodiments. It will be clear to those skilled in the art that modifications and/or variations of the disclosed subject matter can be made without departing from the scope of the invention set forth herein.

We claim:

1. A method of specifically killing of target cells consisting essentially of the steps of:
   (a) activating a culture of leucocytes containing IgG1, IgG2a, IgG2b or IgG3 antibody Fc receptors ex vivo with an amount of interleukin-2 sufficient to enhance the natural killer activity of said cells to form IL-2-activated effector cells;
   (b) separating said effector cells from toxic amounts of interleukin-2;
   (c) binding the Fc receptors of said IL-2-activated effector cells with Fc-containing monoclonal antibodies of class IgG1, IgG2a, IgG2b or IgG3 whose paratopic portions immunoreact with an antigen expressed on the surface of target cells to form armed, IL-2-activated effector cells;
   (d) contacting target cells with a cytotoxic amount of said armed, IL-2-activated effector cells in the absence of exogenous IL-2; and
   (e) maintaining said contact for a time period sufficient for said armed, IL-2-activated effector cells to kill said target cells.

2. The method according to claim 1 wherein said target cells are tumor cells, and said antigen expressed on the surface of said target tumor cells is disialogangliosides GD2 or GD3.

3. The method according to claim 2 wherein said monoclonal antibodies are secreted by the hybridoma having ATCC accession number HB 8890.

4. The method according to claim 2 wherein said monoclonal antibodies are secreted by the hybridoma having ATCC accession number HB 9118.

5. The method of claim 1 further comprising contacting said target cells with a cytotoxic amount of bispecific hybrid monoclonal paratopic molecules that contain a first anti-T3 paratopic portion that immunoreacts with the T3 antigen expressed on the surfaces of T cells and a second paratopic portion that immunoreacts with a second epitope expressed on the surface of the target cells, said second epitope being different from the antigen with which said first-named Fc-containing monoclonal antibodies immunoreact.

6. The method of claim 5 wherein said anti-T3 paratopic portion that immunoreacts with the T3 antigen is secreted by the hybridoma having ATCC accession number CRL 8001.

7. The method of claim 6 wherein said target cells express both disialogangliosides GD2 and GD3, said first-named Fc-containing monoclonal antibodies immunoreact with one of said disialogangliosides, and said second paratopic portions of said hybrid molecule immunoreact with the other of said disialogangliosides.

8. The method of claim 5 wherein said bispecific hybrid molecules are contacted with said target cells substantially simultaneously with the contacting of said target cells with said armed, IL-2-activated effector cells.

9. The method of claim 8 wherein said bispecific hybrid molecules are coated on the surfaces of anti-T3-activated T cells that express the T3 antigen prior to said target cell contacting.

10. The method of claim 9 wherein said anti-T3-activated T cells are formed by the steps of
    (a) admixing and contacting a T cell population containing T3+ T cells with an activating amount of anti-T3 monoclonal antibodies;
    (b) maintaining said contact under biological conditions for a time period sufficient for the concentration of T3+ cells to diminish to about 75 percent of the concentration at the start of the contacting, while the number of cells in the population remains at least about constant to form anti-T3-activated T cells;
    (c) separating said anti-T3-activated T cells from said anti-T3 antibodies; and
    (d) coating said separated anti-T3-activated t cells with said anti-T3-containing bispecific hybrid molecules.

11. A method of enhancing ADCC of tumor cells consisting essentially of the steps of:
    (a) activating a culture of peripheral blood mononuclear cells containing IgG1, IgG2a, IgG2b or IgG3 antibody Fc receptors ex vivo with an amount of interleukin-2 sufficient to enhance the natural killer activity of said cells to form IL-2-activated effector cells;
    (b) separating said IL-2-activated effector cells from toxic amounts of interleukin-2;
    (c) binding the Fc receptors of said IL-2-activated effector cells with Fc-containing monoclonal antibodies of class IgG1, IgG2a, IgG2b or IgG3 whose paratopic portions immunoreact with disialogangliosides GD2 or GD3 to form armed, IL-2-activated effector cells;
    (d) contacting a cytotoxic amount of said armed, IL-2-activated effector cells with tumor cells that express disialoglioside selected from the group consisting of GD2 and GD3 in the absence of exogenous IL-2; and (e) maintaining said contact for a time period sufficient for said armed, IL-2-activated effector cells to lyse said tumor cells.

12. The method of claim 11 wherein said contacting takes place in vitro.

13. The method of claim 11 wherein said contacting takes place in vivo.

14. The method of claim 11 wherein said target cells express both GD2 and GD3, and comprising the additional step of contacting said target cells with a cytotoxic amount of bispecific hybrid monoclonal paratopic molecules that contain first anti-T3 paratopic portions that immunoreact with the T3 antigen expressed on the surfaces of T cells and second paratopic portions that immunoreact with disialoganglioside GD2 or GD3, the ganglioside with which said second paratopic portions react being the disialoganglioside with which said Fc-containing monoclonal antibodies do not immunoreact.

15. The method of claim 14 wherein said anti-T3 paratopic portions of said bispecific hybrid molecules are secreted by the hybridoma having ATCC accession number CRL 8001, said Fc-containing monoclonal antibodies are secreted by a hybridoma selected from the group consisting of those having ATCC accession numbers HB 8890 and HB 9118, and the second paratopic portions of said bispecific hybrids are secreted by a hybridoma selected from the group consisting of those having ATCC accession numbers HB 8890, HB 9118 and HB 8568.

16. A target cell killing composition consisting essentially of an aqueous physiologically tolerable diluent medium free of exogenous IL-2, containing dispersed therein an amount of armed, IL-2-activated effector cells from a leucocyte population effective to kill target cells, said IL-2-activated effector cells being armed with monoclonal antibodies of class IgG1l IgG2a, IgG2b or IgG3 bound to the Fc receptors of said cells, the paratopic portions of said monoclonal antibodies immunoreacting with an antigen expressed on the surfaces of said target cells.

17. The composition of claim 16 wherein said target cells express disialogangliosides GD2 or GD3 on their cell surfaces.

18. The composition of claim 17 wherein said monoclonal antibodies are secreted by a hybridoma having the ATCC accession number HB 8890 or HB 9118.

19. The composition of claim 16 further including a cytotoxic amount of bispecific hybrid paratopic molecules that contain first anti-T3 paratopic portions that immunoreact with the T3 antigen expressed on the surfaces of T cells and second paratopic portions that immunoreact with a second epitope expressed on the surfaces of said target cells, said second target cell epitope being different from the antigen with which said first-named monoclonal antibodies immunoreact.

20. The composition of claim 19 wherein said bispecific hybrid paratopic molecules of said composition are present coated on the surfaces of anti-T3-activated T cells as armed, anti-T3-activated T cells along with said armed, IL-2-activated effector cells.

* * * * *